United States Patent
Basilion et al.

(10) Patent No.: US 10,363,313 B2
(45) Date of Patent: *Jul. 30, 2019

(54) PSMA LIGANDS AND USES THEREOF

(71) Applicant: CASE WESTERN RESERVE UNIVERSITY, Cleveland, OH (US)

(72) Inventors: James Basilion, Shaker Heights, OH (US); Xinning Wang, Cleveland, OH (US); Clemens Burda, Cleveland Heights, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/895,855

(22) Filed: Feb. 13, 2018

(65) Prior Publication Data
US 2018/0369385 A1 Dec. 27, 2018

Related U.S. Application Data

(63) Continuation of application No. 14/767,984, filed as application No. PCT/US2014/016932 on Feb. 18, 2014, now Pat. No. 9,889,199.

(60) Provisional application No. 61/765,346, filed on Feb. 15, 2013.

(51) Int. Cl.
| | | |
|---|---|---|
| *A61K 47/18* | (2017.01) | |
| *A61N 5/06* | (2006.01) | |
| *A61K 31/695* | (2006.01) | |
| *A61K 41/00* | (2006.01) | |
| *A61K 49/00* | (2006.01) | |
| *A61K 47/64* | (2017.01) | |
| *A61K 49/04* | (2006.01) | |
| *A61K 47/65* | (2017.01) | |
| *A61K 47/60* | (2017.01) | |
| *A61K 47/69* | (2017.01) | |
| *A61K 9/00* | (2006.01) | |

(52) U.S. Cl.
CPC ............ *A61K 47/18* (2013.01); *A61K 9/0019* (2013.01); *A61K 31/695* (2013.01); *A61K 41/0071* (2013.01); *A61K 47/60* (2017.08); *A61K 47/64* (2017.08); *A61K 47/65* (2017.08); *A61K 47/6929* (2017.08); *A61K 49/0034* (2013.01); *A61K 49/0052* (2013.01); *A61K 49/0423* (2013.01); *A61N 5/062* (2013.01)

(58) Field of Classification Search
CPC .............. A61K 47/18; A61K 47/48215; A61K 47/48884; A61K 9/0019; A61K 31/695; A61K 49/0052; A61N 5/062

See application file for complete search history.

(56) References Cited

U.S. PATENT DOCUMENTS

| | | | |
|---|---|---|---|
| 9,889,199 B2* | 2/2018 | Basilion | A61K 49/0034 |
| 2008/0193381 A1 | 8/2008 | Babich et al. | |
| 2009/0061010 A1 | 3/2009 | Zale et al. | |
| 2010/0324008 A1* | 12/2010 | Low | A61K 49/0041 |
| | | | 514/184 |

FOREIGN PATENT DOCUMENTS

| | | |
|---|---|---|
| WO | 2008/057437 A1 | 5/2008 |
| WO | 2011/106639 A1 | 9/2011 |
| WO | 2012/106713 A2 | 8/2012 |

OTHER PUBLICATIONS

Extended European Search Report for Application No. 14751113.3-1453/2958596 dated Oct. 10, 2016.
Sumith A. Kularatne et al: "Synthesis and Biological Analysis of Prostate-Specific Membrane Antigen-Targeted Anticancer Prodrugs", Journal of Medicinal Chemistry, vol. 53, No. 21, Nov. 11, 2010 (Nov. 11, 2010), pp. 7767-7777, XP055103918.
Ikeda et al., Chem. Sci., (2010), 1, p. 491-498.
EP Office action for Application No. 14751113.3-1109, dated Jan. 1, 2019.

* cited by examiner

*Primary Examiner* — Yong L Chu

(74) *Attorney, Agent, or Firm* — Tarolli, Sundheim, Covell & Tummino LLP

(57) ABSTRACT

Compounds that are PSMA ligands, pharmaceutical compositions comprising these compounds, methods for treating and detecting cancers in a subject, methods for identifying cancer cells in a sample are described herein.

9 Claims, 6 Drawing Sheets

Figs. 3A-C

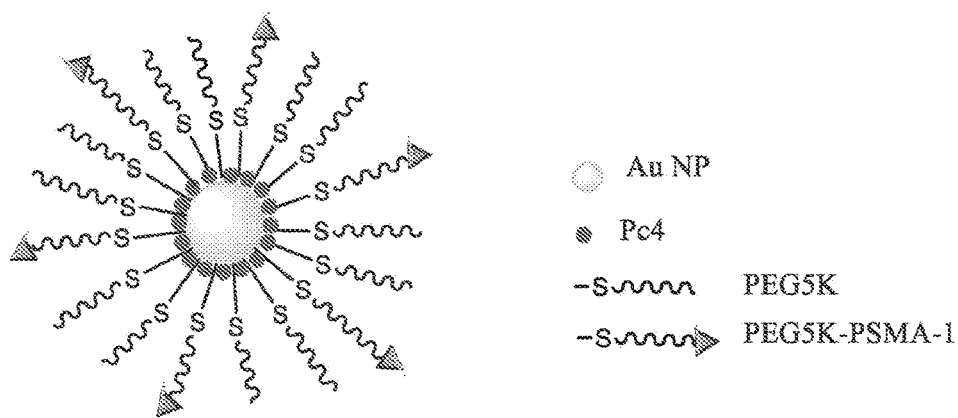
Fig. 4
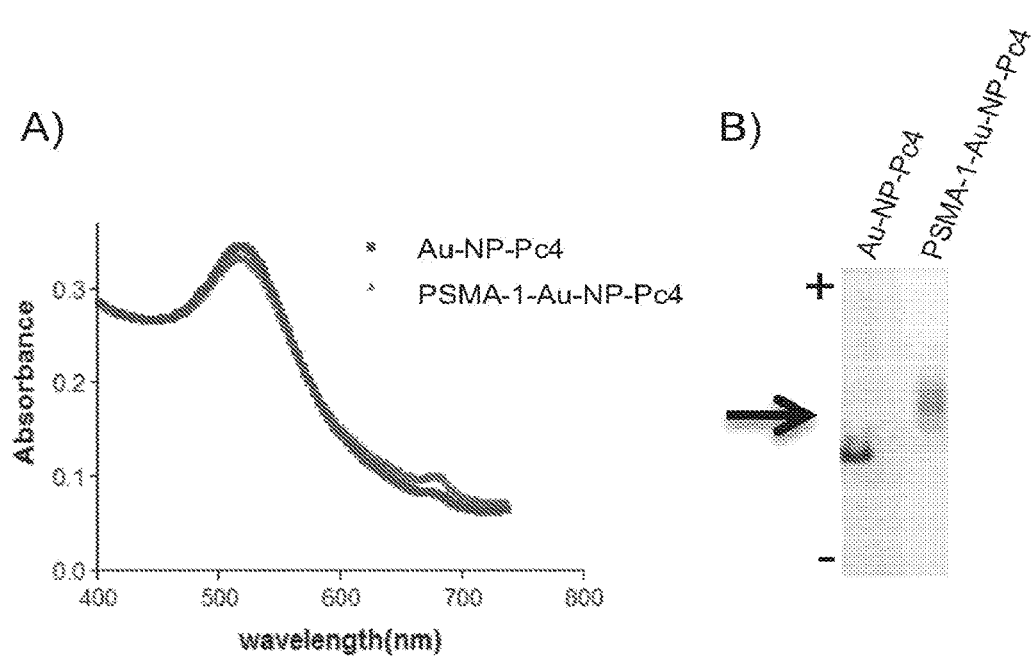
Figs. 5A-B

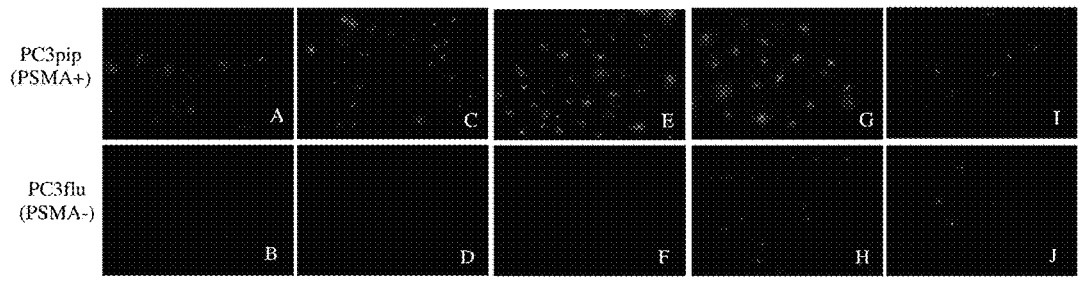
Figs. 8A-J
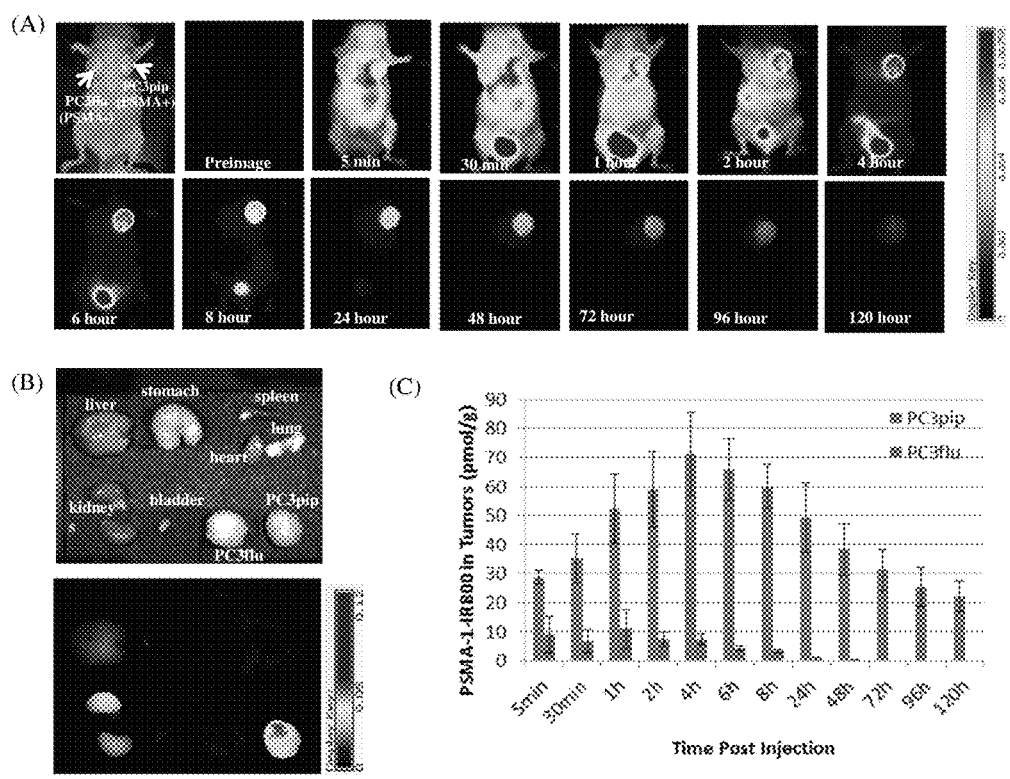
Figs. 9A-C

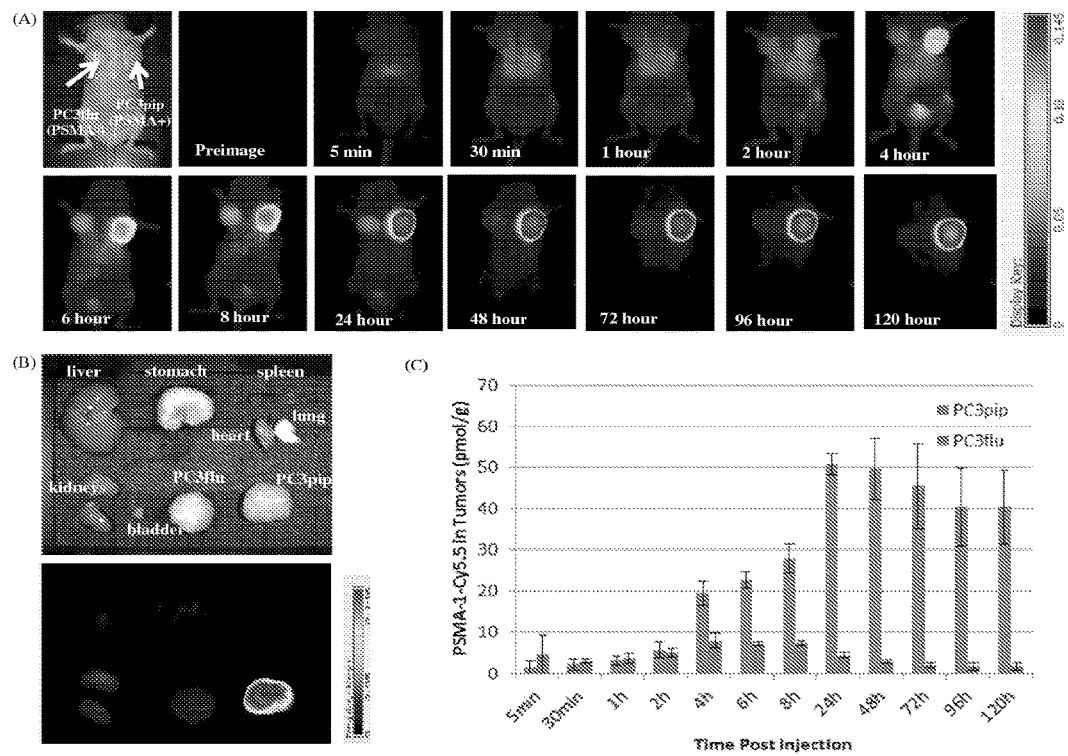
Figs. 10A-C
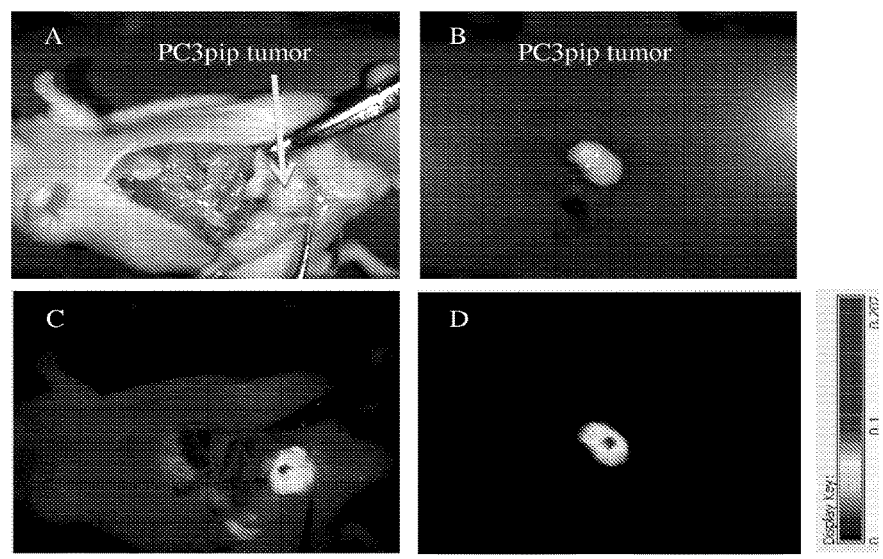
Figs. 11A-D

PSMA LIGANDS AND USES THEREOF

RELATED APPLICATION

This application is a continuation of U.S. application Ser. No. 14/767,984, filed, Feb. 18, 2014, now U.S. Pat. No. 9,889,199, which claims priority from U.S. Provisional Application No. 61/765,346, filed Feb. 15, 2013, the subject matter of which is incorporated herein by reference in their entirety.

TECHNICAL FIELD

This application relates to prostate-specific membrane antigen (PSMA) ligands and to their use in compositions for targeting, imaging, and treating cancer.

BACKGROUND

Prostate-specific membrane antigen (PSMA) is a 120 kDa protein expressed in prostate tissues and was originally identified by reactivity with a monoclonal antibody designated 7E11-C5 (Horoszewicz et al., 1987, Anticancer Res. 7:927-935; U.S. Pat. No. 5,162,504). PSMA is characterized as a type II transmembrane protein sharing sequence identity with the transferrin receptor (Israeli et al., 1994, Cancer Res. 54:1807-1811). PSMA is a glutamate carboxy-peptidase that cleaves terminal carboxy glutamates from both the neuronal dipeptide N-acetylaspartylglutamate (NAAG) and gamma-linked folate polyglutamate. That is, expression of PSMA cDNA confers the activity of N-acetylated α-linked acidic dipeptidase or "NAALADase" activity (Carter et al., 1996, PNAS 93:749-753).

PSMA is expressed in increased amounts in prostate cancer, and elevated levels of PSMA are also detectable in the sera of these patients (Horoszewicz et al., 1987, supra; Rochon et al., 1994, Prostate 25:219-223; Murphy et al., 1995, Prostate 26:164-168; and Murphy et al., 1995, Anticancer Res. 15:1473-1479). As a prostate carcinoma marker, PSMA is believed to serve as a target for imaging and cytotoxic treatment modalities for prostate cancer. Prostate carcinogenesis, for example, is associated with an elevation in PSMA abundance and enzymatic activity of PSMA. PSMA antibodies, particularly indium-111 labeled and tritium labeled PSMA antibodies, have been described and examined clinically for the diagnosis and treatment of prostate cancer. PSMA is expressed in prostatic ductal epithelium and is present in seminal plasma, prostatic fluid and urine.

Recent evidence suggests that PSMA is also expressed in tumor associated neovasculature of a wide spectrum of malignant neoplasms including conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma. (Chang et al. (1999) Cancer Res. 59, 3192-3198).

SUMMARY

Embodiments described herein relate to compounds that are PSMA ligands, pharmaceutical compositions comprising these compounds, methods for treating and detecting cancers (e.g., prostate cancer) in a subject using these compounds, and methods for identifying cancer cells (e.g., prostate cancer cells) in a sample using these compounds.

In some embodiments, the compound can include the general formula (I):

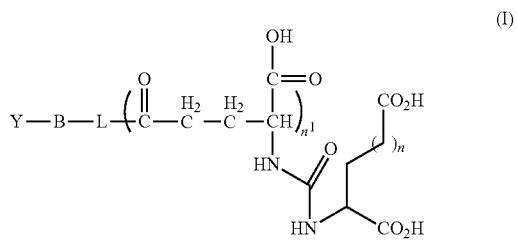

wherein:

n and $n^1$ are each independently 1, 2, 3, or 4;

L is an optionally substituted aliphatic or heteroaliphatic linking group;

B comprises at least one negatively charged amino acid; and

Y is a H of B or can include at least one of a detectable moiety, therapeutic agent, or a theranostic agent that is directly or indirectly linked to B. In other embodiments, Y can be selected from the group consisting of an imaging agent, anticancer agent, or combination thereof.

In some embodiments, L can include at least one ring selected from the group consisting of an optionally substituted 4 to 7 membered nonaromatic heterocyclic ring and an optionally substituted C4-C7 cycloalkyl ring.

In some embodiments, B has the following formula:

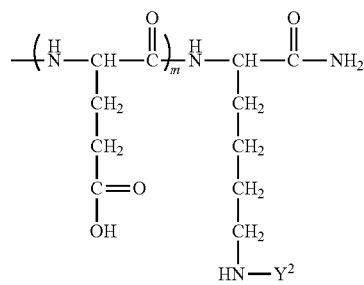

wherein m is 1, 2, 3, or 4, $X^1$ is an amino acid, and $Y^1$ is a H of $X^1$ or include at least one of an amino acid, peptide, detectable moiety, therapeutic agent, or theranostic agent that is directly or indirectly linked to $X^1$.

In other embodiments, B has the following formula:

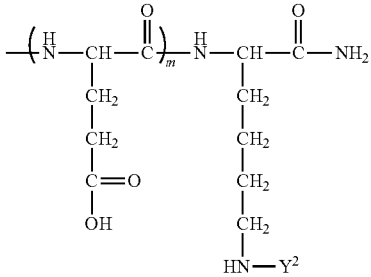

wherein m is 1, 2, 3, or 4 and $Y^2$ is a H or can include at least one of an amino acid, peptide, detectable moiety, therapeutic agent, or theranostic agent.

In other embodiments, the compound can have the general formula:

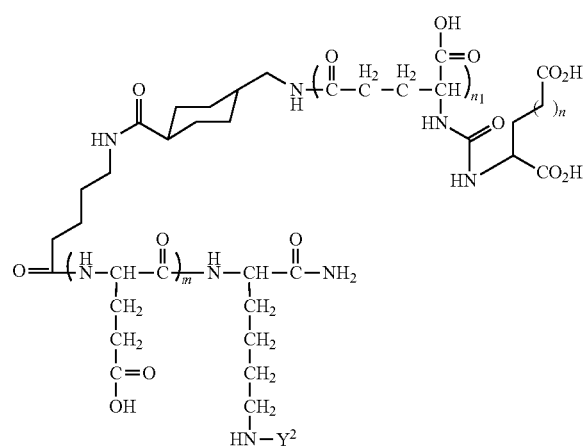

wherein m, n, and $n^1$ are each independently 1, 2, 3, or 4; and $Y^2$ is a H or can include at least one of an amino acid, peptide, detectable moiety, therapeutic agent, or theranostic agent.

In some embodiments, the cancer that is treated and/or detected is prostate cancer. In other embodiments, the cancer that is treated and/or detected can include malignant neoplasms, such as conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

Other embodiments described herein relate to a composition for treating cancer, such as prostate cancer, in a subject. The composition can include a polyethylene glycolylated (PEGylated) nanoparticle, at least one anti-cancer agent coupled to the surface of the nanoparticle, and at least one prostate specific membrane antigen (PSMA) ligand coupled to polyethylene glycol of the nanoparticle for targeting the composition to a cancer cell expressing PSMA, such as a prostate cancer cell. The PSMA ligand can include the general formula (I):

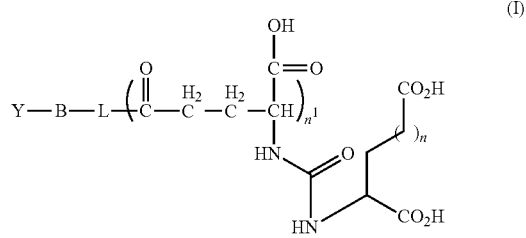

where:
n and $n^1$ are each independently 1, 2, 3, or 4;
L is an optionally substituted aliphatic or heteroaliphatic linking group;
B comprises at least one negatively charged amino acid; and
Y is the PEGylated nanoparticle that is directly or indirectly linked to B.

In some embodiments, the anti-cancer agent can include Phthalocyanine 4. The polyethylene glycolylated (PEGylated) nanoparticle can be a polyethylene glycolylated (PEGylated) gold nanoparticle.

Still other embodiments relate to a method of treating cancer, such as prostate cancer, in a subject. The method includes administering systemically to the subject with cancer a therapeutically effective amount of a composition that includes PEGylated gold nanoparticles, Phthalocyanine 4 conjugated to the PEGylated gold nanoparticle; and at least one prostate specific membrane antigen (PSMA) ligand coupled to polyethylene glycol of the nanoparticle for targeting the composition to a prostate cancer cell. The PSMA ligand includes the general formula (I):

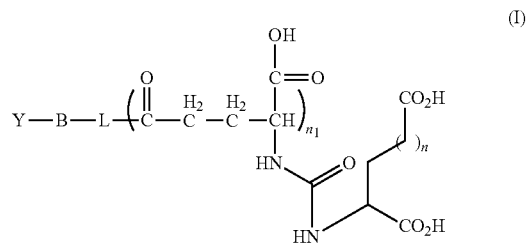

where:
n and $n^1$ are each independently 1, 2, 3, or 4;
L is an optionally substituted aliphatic or heteroaliphatic linking group;
B comprises at least one negatively charged amino acid; and
Y is the PEGylated nanoparticle that is directly or indirectly linked to B. After systemic administration of the composition to the subject, the cancer cell is exposed to light effective to induce the cytotoxic effects of Phthalocyanine 4.

BRIEF DESCRIPTION OF THE DRAWINGS

FIG. 4 is a shematic representation of PSMA-targeted gold nanoparticles in accordance with an embodiment. PEG5K=polyethylene glycol, 5000 daltons. PEG5K-PSMA-1=polyethylene glycol derivatized with PSMA-1 ligand. (figure not to scale)

FIGS. 5(A-B) illustrate: A) UV absorption spectra of nanoparticles. Gold nanoparticles absorb at 520 nm and Pc4 absorbs at 678 nm. B) Agarose gel electrophoresis of nanoparticles. Arrow indicates migration of targeted nanoparticles.

FIGS. 8(A-J) illustrate images showing in vitro uptake results of PSMA-1-Cy5.5 by fluorescence microscopy. PSMA positive PC3pip cells and PSMA negative cells on coverslips were incubated with 1 µM of PSMA-1-Cy5.5 for 15 min (A-B), 30 min (C-D), 1 hour (E-F) and 4 hours (G-H). Selective uptake was observed in PC3pip cells. Specificity of PSMA-1-Cy5.5 to PSMA was evaluated by incubation of PC3pip (I) and PC3flu (J) cells with 1 µM of PSMA-1-Cy5.5 and 10 µM of ZJ24. Signal in PC3pip cells was significantly block by ZJ24, suggestion the binding of PSMA-1-Cy5.5 to PSMA is specific.

FIGS. 9(A-C) illustrate imaging of PSMA-1-IR800 in mice bearing flank PC3pip and PC3flu tumors. (A) In vivo Maestro imaging of PSMA-1-IR800. Mice were received 1 nmol of PSMA-1-IR800 through tail vein injection, then imaging as designated time. Representative images are shown. Selective uptake in PC3pip tumors was observed. Highest PC3pip tumor uptake was observed four hours post injection. (B) Ex vivo imaging of mice organs at 120 hours post injection of PSMA-1-IR800. The fluorescent signal in PC3pip tumor was significantly higher than in other organs. (C) FMT 3D quantification of PSMA-1-IR800 in PC3pip and PC3flu tumors. Values represent mean±SD of 5 animals.

FIGS. 10(A-C) illustrate images and graph showing PSMA-1-Cy5.5 in mice bearing flank PC3pip and PC3flu tumors. (A) In vivo Maestro imaging of PSMA-1-Cy5.5. Mice were received 1 nmol of PSMA-1-Cy5.5 through tail vein injection, then imaging as designated time. Representative images are shown. Selective uptake in PC3pip tumors was observed. Highest PC3pip tumor uptake was observed twenty-four hours post injection. (B) Ex vivo imaging of mice organs at 120 hours post injection of PSMA-1-Cy5.5. The fluorescent signal in PC3pip tumor was significantly higher than in other organs. (C) FMT 3D quantification of PSMA-1-Cy5.5 in PC3pip and PC3flu tumors. Values represent mean±SD of 5 animals.

FIGS. 11 (A-D) illustrate images showing PSMA-1-Cy5.5 can selectively target othotopic PSMA positive PC3pip tumors. Mice were received 1 nmol of PSMA-1-Cy5.5 through tail vein injection. Twenty-four hours post injection, mice were sacrificed, the abdomen was opened to expose tumor and then imaged. Representative images are shown. (A) Black and white image of mice with othotopic PC3pip tumor. The location of PC3pip tumor was indicated by arrow. (B) In vivo Maestro imaging of PSMA-1-Cy5.5 in mice bearing othotopic PC3pip tumors. Selective uptake in othotopic PC3pip tumors was observed. (C) Black and white imagine of PC3pip tumor. (D) Ex vivo Maestro imaging of PC3pip tumor at 24 hours post injection of PSMA-1-Cy5.5. Bright fluorescent signal was observed in PC3pip tumor.

DETAILED DESCRIPTION

Figure 1:
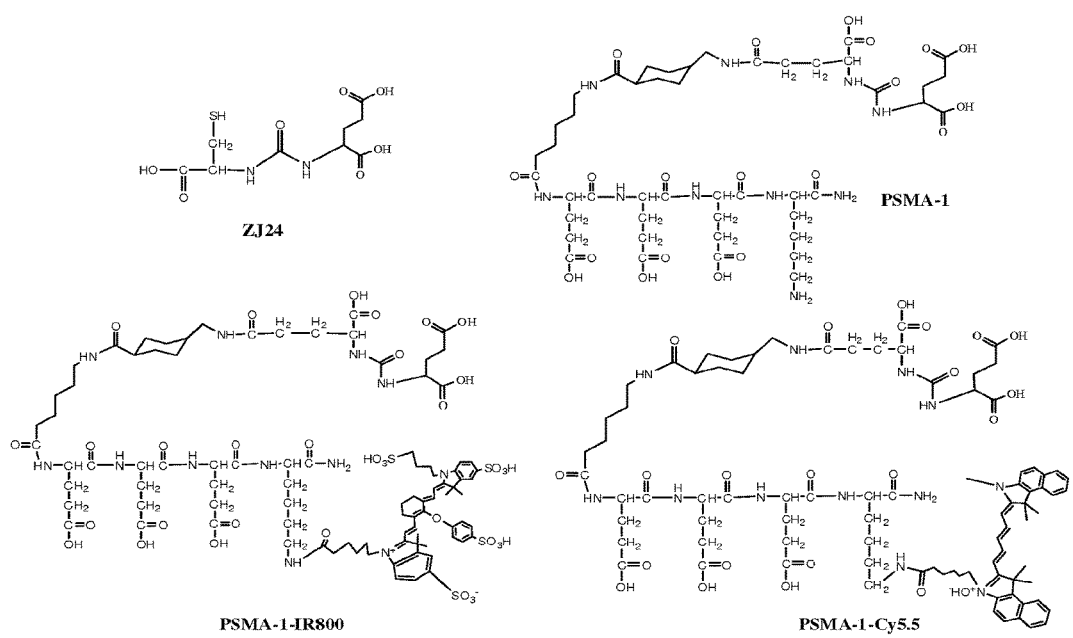
FIG. 1 illustrates structures of PSMA ligands.

All scientific and technical terms used in this application have meanings commonly used in the art unless otherwise specified. The definitions provided herein are to facilitate understanding of certain terms used frequently herein and are not meant to limit the scope of the application.

The articles "a" and "an" are used herein to refer to one or to more than one (i.e., to at least one) of the grammatical object of the article. By way of example, "an element" means one element or more than one element.

As used herein, the term "sample" can refer to a specimen or culture obtained from any source, as well as clinical, research, biological and environmental samples. Biological samples may be obtained from animals (including humans) and encompass cells, fluids, solids, tissues, and organs, and whole organisms.

As used herein, the term "subject" can refer to any animal including, but not limited to, humans and non-human animals (e.g., rodents, arthropods, insects, fish (e.g., zebrafish)), non-human primates, ovines, bovines, ruminants, lagomorphs, porcines, caprines, equines, or canines felines, aves, etc.).

As used herein, the terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

As used herein, the term "polynucleotide" can refer to oligonucleotides, nucleotides, or to a fragment of any of these, to DNA or RNA (e.g., mRNA, rRNA, tRNA) of genomic or synthetic origin, which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids, i.e., oligonucleotides, containing known analogues of natural nucleotides. The term can also encompass nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term can also include peptides and polypeptide fragments, motifs and the like, glycosylated polypeptides, and all "mimetic" and "peptidomimetic" polypeptide forms.

"PSMA" refers to Prostate Specific Membrane Antigen, a potential carcinoma marker that has been hypothesized to serve as a target for imaging and cytotoxic treatment modalities for cancer.

As used herein, the term "small molecule" can refer to lipids, carbohydrates, polynucleotides, polypeptides, or any other organic or inorganic molecules.

As used herein, the term "imaging probe" can refer to a biological or chemical moiety that may be used to detect, image, and/or monitor the presence and/or progression of a cell cycle, cell function/physiology, condition, pathological disorder and/or disease.

As used herein, the terms "treating" or "treatment" of a disease can refer to executing a treatment protocol to eradicate at least one diseased cell. Thus, "treating" or "treatment" does not require complete eradication of diseased cells.

As used herein, the term "nanoparticle" refers to any particle having a diameter of less than 1000 nanometers (nm). In some embodiments, nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that are used in various embodiments. In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

As used herein, an "effective amount" can refer to that amount of a therapeutic agent that results in amelioration of symptoms or a prolongation of survival in the subject and relieves, to some extent, one or more symptoms of the disease or returns to normal (either partially or completely) one or more physiological or biochemical parameters associated with or causative of the disease.

As used herein, therapeutic agents can include any agent (e.g., molecule, drug, pharmaceutical composition, etc.) capable of preventing, inhibiting, or arresting the symptoms and/or progression of a disease.

Embodiments described herein relate to PSMA ligands or compounds that are PSMA ligands, as well as pharmaceutical compositions comprising these compounds, methods for treating and detecting cancers, such as prostate cancer, in a subject using these compounds, and methods for identifying cancer cells in a sample using these compounds.

Pathological studies indicate that PSMA is expressed by virtually all prostate cancers, and its expression is further increased in poorly differentiated, metastatic, and hormone-refractory carcinomas. Higher PSMA expression is also found in cancer cells from castration-resistant prostate cancer patients. Increased PSMA expression is reported to correlate with the risk of early prostate cancer recurrence after radical prostatectomy. In addition to being overexpressed in prostate cancer (PCa), PSMA is also expressed in the neovasculature of neoplasms including but not limited to conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma.

In some embodiments, the compounds described herein, which are PSMA ligands, can selectively recognize PSMA-expressing tumors, cancer cells, and/or cancer neovasculature in vivo and be used to deliver a therapeutic agent, detectable moiety, and/or theranostic agent to the PSMA-expressing tumors, cancer cells, and/or cancer neovasculature to treat and/or detect the PSMA-expressing tumors, cancer cells, and/or cancer neovasculature in a subject.

In some embodiments, the PSMA expressing cancer that is treated and/or detected is prostate cancer. In other embodiments, the cancer that is treated and/or detected can include malignant neoplasms, such a conventional (clear cell) renal carcinoma, transitional cell carcinoma of the urinary bladder, testicular embryonal carcinoma, colonic adenocarcinoma, neuroendocrine carcinoma, gliobastoma multiforme, malignant melanoma, pancreatic ductal carcinoma, non-small cell lung carcinoma, soft tissue carcinoma, breast carcinoma, and prostatic adenocarcinoma In some embodiments, the compound can include a PSMA ligand that has the general formula (I):

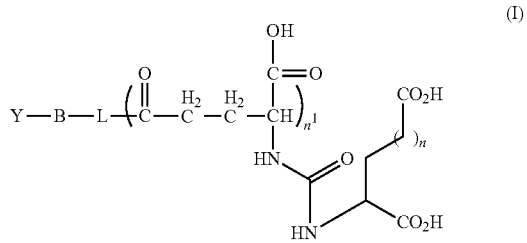

wherein:
n and $n^1$ are each independently 1, 2, 3, or 4;
L is an optionally substituted aliphatic or heteroaliphatic linking group;

B comprises at least one negatively charged amino acid; and

Y is a H of B or can include at least one of a detectable moiety, therapeutic agent, or a theranostic agent that is directly or indirectly linked or coupled to B. In other embodiments, Y can be selected from the group consisting of an imaging agent, anticancer agent, or combination thereof.

In other embodiments, L can be an optionally substituted aliphatic or heteroaliphatic group that includes at least one ring selected from the group consisting of an optionally substituted 4 to 7 membered nonaromatic heterocyclic ring and an optionally substituted C4-C7 cycloalkyl ring.

An aliphatic group is a straight chained, branched or cyclic non-aromatic hydrocarbon, which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group (preferably C1-C4 straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

Suitable optional substituents for a substitutable atom in alkyl, cycloalkyl, aliphatic, cycloaliphatic, heterocyclic, benzylic, aryl, or heteroaryl groups described herein are those substituents that do not substantially interfere with the activity of the disclosed compounds. A "substitutable atom" is an atom that has one or more valences or charges available to form one or more corresponding covalent or ionic bonds with a substituent. For example, a carbon atom with one valence available (e.g., —C(—H)═) can form a single bond to an alkyl group (e.g., —C(-alkyl)═), a carbon atom with two valences available (e.g., —C(H$_2$)—) can form one or two single bonds to one or two substituents (e.g., —C(alkyl)(Br))—, —C(alkyl)(H)—) or a double bond to one substituent (e.g., —C═O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —POR$^a$R$^b$, PO$_2$R$^a$R$^b$, —PO$_3$R$^a$R$^b$, —PO$_4$R$^a$R$^b$, —P(S)R$^a$R$^b$, —P(S)OR$^a$R$^b$, —P(S)O$_2$R$^a$R$^b$, —P(S)O$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CRC═CR$^a$R$^b$, —C═CR$^a$, ═O, ═S, ═CR$^a$R$^b$, ═NR$^a$, ═NOR$^a$, ═NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$—R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group. Also contemplated are isomers of these groups.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counter anions are provided in the section below directed to suitable pharmacologically acceptable salts.

In other embodiments, B can include at least one, two, three, four, or more negatively charged amino acids, i.e., amino acids with a negative charged side chain, such as glutamic acid, aspartic acid, and/or tyrosine. B can also include other amino acids that facilitate binding of B to Y and/or the PSMA ligand to a detectable moiety, therapeutic agent, and/or theranostic agent.

In some embodiments, B can have the following formula:

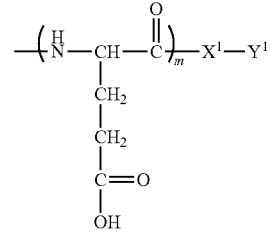

wherein m is 1, 2, 3, or 4, X$^1$ is an amino acid, and Y$^1$ is a H of X$^1$ or includes at least one of an amino acid, peptide, detectable moiety, therapeutic agent, or theranostic agent that is directly or indirectly linked to X$^1$.

In certain embodiments, X$^1$ can facilitate binding of B to Y and/or the PSMA ligand to a detectable moiety, therapeutic agent, and/or theranostic agent.

In other embodiments, B can have the following formula:

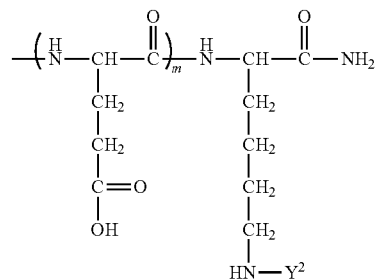

wherein m is 1, 2, 3, or 4 and $Y^2$ is a H or can include at least one of an amino acid, peptide, detectable moiety, therapeutic agent, or theranostic agent.

In other embodiments, the compound can have the general formula:

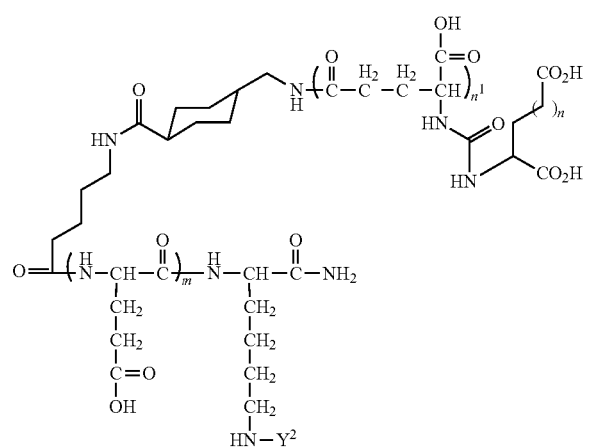

wherein m, n, and $n^1$ are independently 1, 2, 3, or 4; and $Y^2$ is a H or can include at least one of an amino acid, peptide, detectable moiety, therapeutic agent, or theranostic agent.

In some embodiments, Y, $Y^1$, or $Y^2$ can be a detectable moiety that is directly or indirectly coupled to B or the PSMA ligand. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, chelating groups, and biotin, dioxigenin or other haptens and proteins for which antisera or monoclonal antibodies are available.

In some embodiments, radionuclides can include atomic isotopes such as $^{99m}Tc$, $^{111}In$, $^{123}I$, $^{124}I$, $^{131}I$, $^{67}Ga$, $^{201}Tl$, $^{125}I$, $^{18}F$, $^{11}C$, $^{76}Br$, $^{124}I$, $^{68}Ga$, $^{82}Rb$, $^{13}N$, $^{64}Cu$, $^{90}Y$, $^{188}Rh$, T (tritium), $^{32}P$, $^{35}S$, $^{153}Sm$, $^{89}Sr$, $^{211}At$, and $^{89}Zr$. These isotopes can be directly or indirectly coupled to the PSMA ligand.

Fluorescence labeling agents or infrared labeling agents include those known to the art, many of which are commonly commercially available, such as ALEXA 350, PACIFIC BLUE, MARINA BLUE, ACRIDINE, EDANS, COUMARIN, BODIPY 493/503, CY2, BODIPY FL-X, DANSYL, ALEXA 488, FAM, OREGON GREEN, RHODAMINE GREEN-X, TET, ALEXA 430, CAL GOLD, BODIPY R6G-X, JOE, ALEXA 532, VIC, HEX, CAL ORANGE™, ALEXA 555, BODIPY 564/570, BODIPY TMR-X, QUASAR™ 570, ALEXA 546, TAMRA, RHODAMINE RED-X, BODIPY 581/591, CY3.5, CY5.5, ROX, ALEXA 568, CAL RED, BODIPY TR-X, ALEXA 594, BODIPY 630/650-X, PULSAR 650, BODIPY 630/665-X, ALEXA 647, IR700, IR800, and QUASAR 670. Fluorescence labeling agents can include other known fluorophores, or proteins known to the art, for example, green fluorescent protein. The fluorescence labeling agents can be directly or indirectly coupled to the PSMA ligands, administered to a subject or a sample, and the subject/sample examined by fluorescence spectroscopy or imaging to detect the labeled compound.

Chelating groups (with or without a chelated metal group) can include those disclosed in U.S. Pat. No. 7,351,401, which is herein incorporated by reference in its entirety.

Near infrared imaging groups are disclosed in, for example, Tetrahedron Letters 49(2008) 3395-3399; Angew. Chem. Int. Ed. 2007, 46, 8998-9001; Anal. Chem. 2000, 72, 5907; Nature Biotechnology vol 23, 577-583; Eur Radiol (2003) 13: 195-208; and Cancer 67: 1991 2529-2537, which are herein incorporated by reference in their entirety.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The PSMA ligands described herein can be coupled to the quantum dots, administered to a subject or a sample, and the subject/sample examined by spectroscopy or imaging to detect the labeled compound.

Magnetic resonance imaging (MRI) contrast agents, can include positive contrast agents and negative contrast agents. The PSMA ligands described herein can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iro, or the like. Typical contrast agents include gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In some embodiments, a PSMA ligand that is coupled to a fluorescence labeling agent or infrared agent can have the following formula:

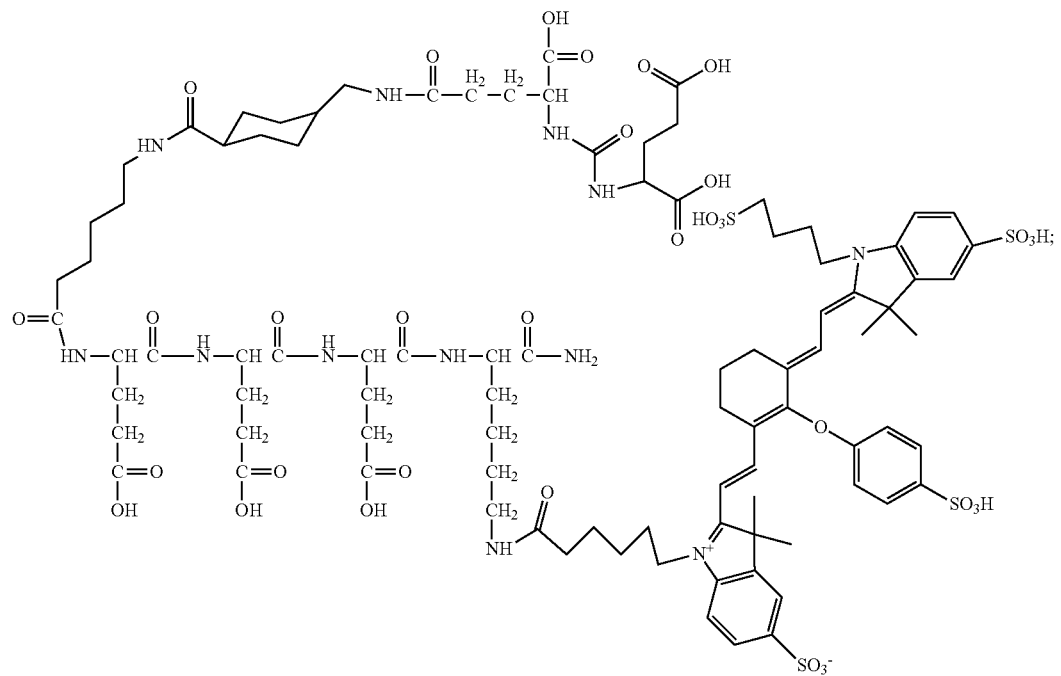
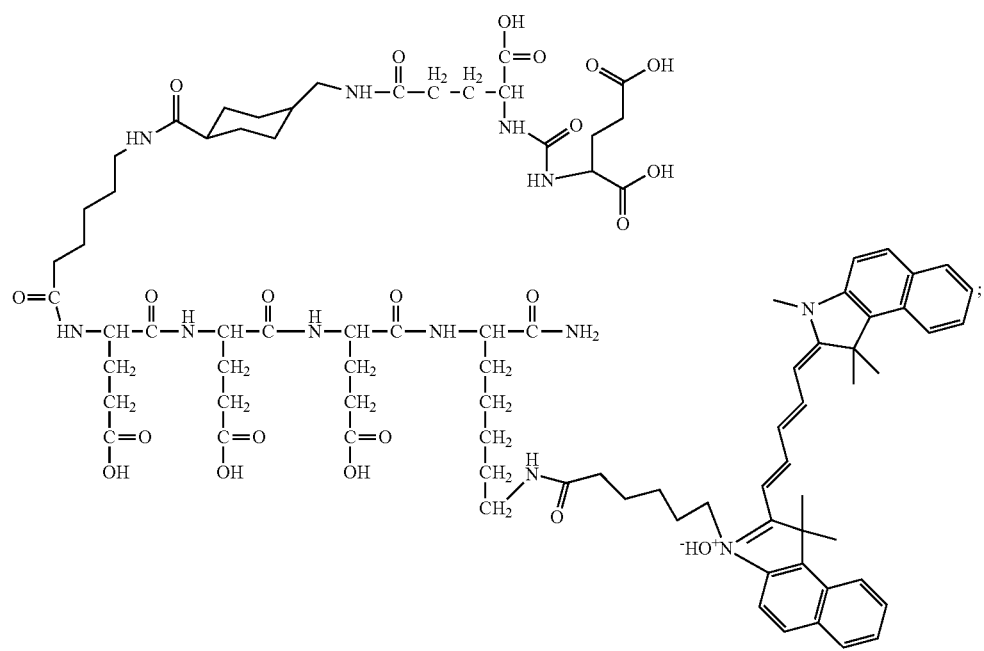

-continued
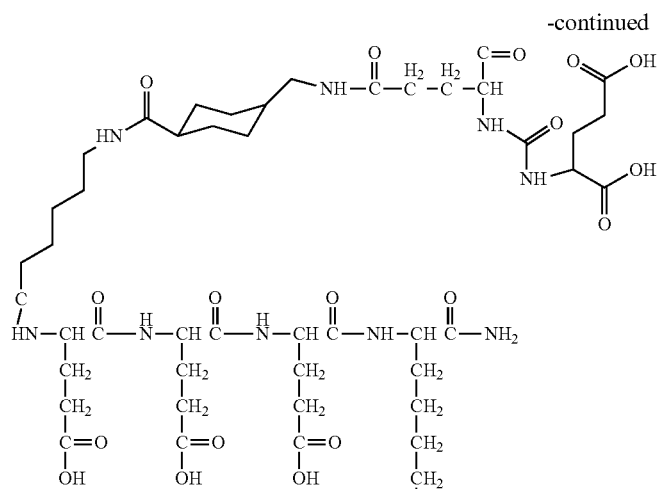
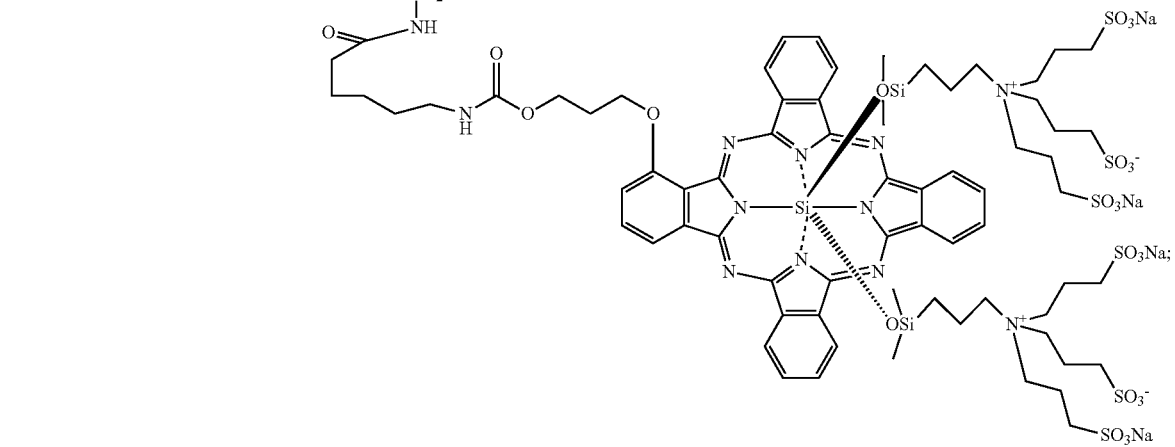
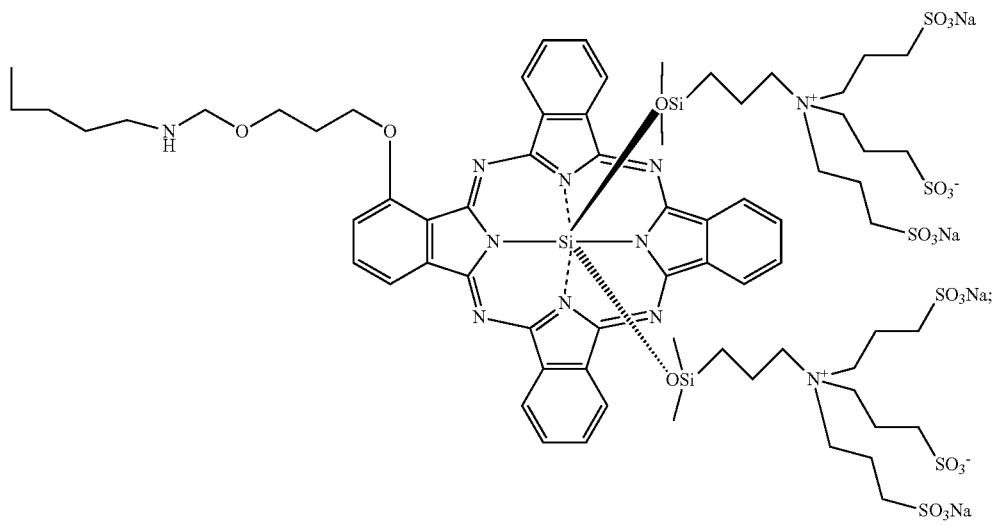

-continued
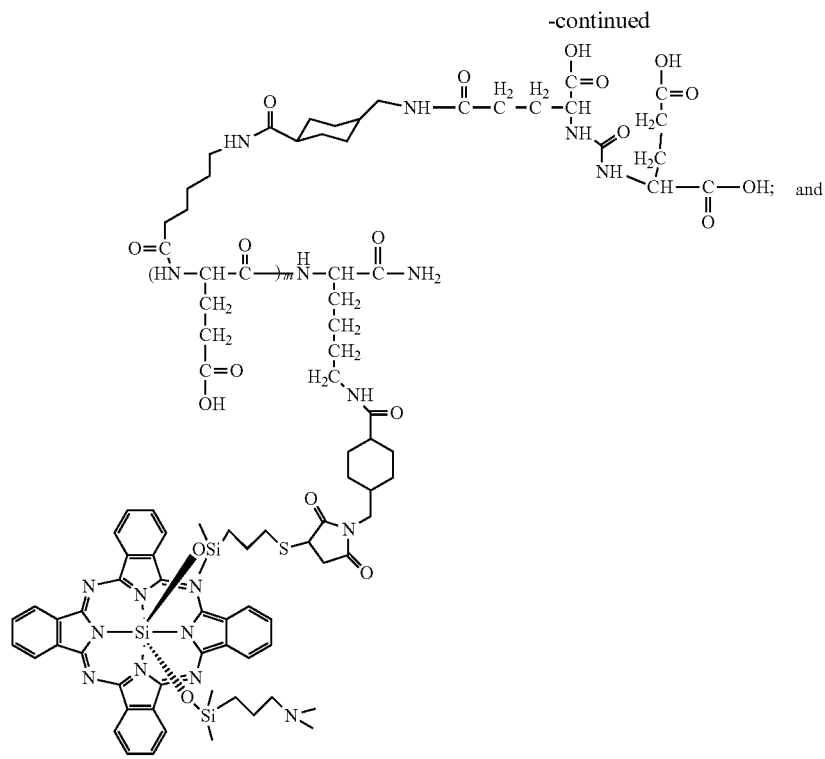
and
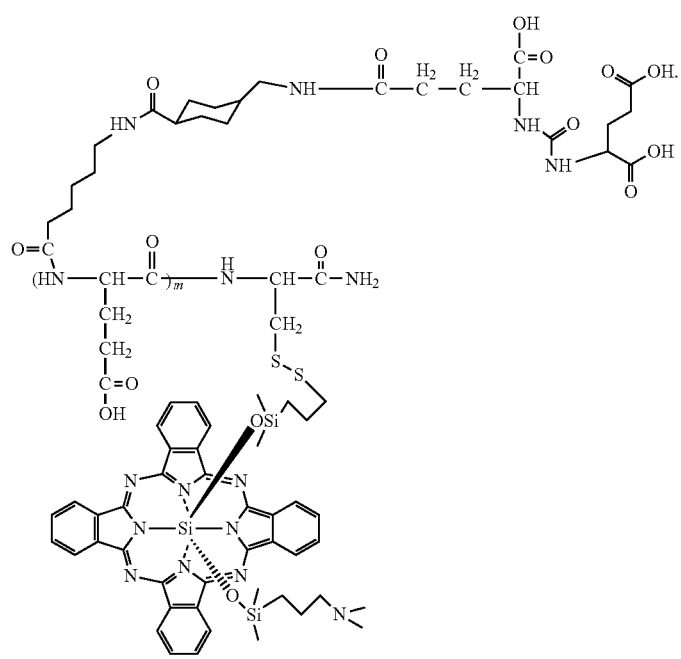

In other embodiments, a PSMA ligand that is coupled to a radiolabel can have the following formula.

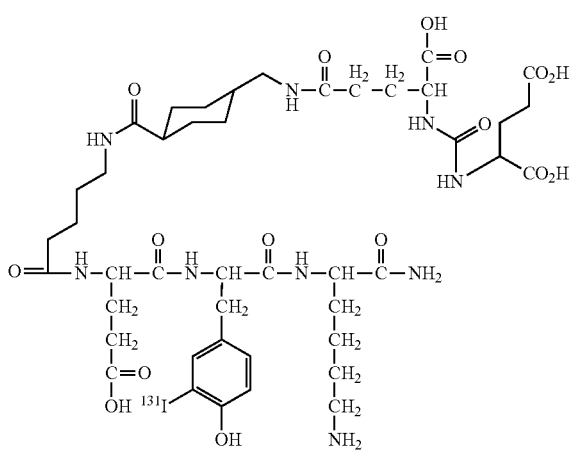 [SMILES: NCCCCC(NC(=O)C(Cc1ccc(O)c([131I])c1)NC(=O)C(CCC(=O)O)NC(=O)CCCCNC(=O)C1CCC(CNC(=O)CCC(NC(=O)NC(CCC(=O)O)C(=O)O)C(=O)O)CC1)C(N)=O]

This PSMA ligand can be prepared by switching out a glutamic acid for a tyrosine residue in a PSMA ligand, which then allows for iodination of the tyrosine using, for example, chloramines T. Alternatively, the three glutamates and lysine of the PSMA ligand can be maintained and Boltman-Hunter chemistry can be used to attach an aromatic to the amine on the lys amino acid and then label it with iodine.

In some aspects, the PSMA ligands coupled to a detectable moiety described herein may be used in conjunction with non-invasive imaging techniques for in vivo imaging, such as magnetic resonance spectroscopy (MRS) or imaging (MRI), or gamma imaging, such as positron emission tomography (PET) or single-photon emission computed tomography (SPECT), to determine the location or distribution of cancer cells. The term "in vivo imaging" refers to any method, which permits the detection of a labeled PSMA ligand, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

For purposes of in vivo imaging, the type of detection instrument available is a major factor in selecting a given detectable moiety. For instance, the type of instrument used will guide the selection of the stable isotope. The half-life should be long enough so that it is still detectable at the time of maximum uptake by the target, but short enough so that the host does not sustain deleterious effects.

The PSMA ligands coupled to a detectable moiety described herein can be administered to the subject by, for example, systemic, topical, and/or parenteral methods of administration. These methods include, e.g., injection, infusion, deposition, implantation, or topical administration, or any other method of administration where access to the tissue desired. In one example, administration can be by intravenous injection in the subject. Single or multiple administrations of the probe can be given. "Administered", as used herein, means provision or delivery is in an amount(s) and for a period of time(s) effective to label cancer cells in the subject.

The PSMA ligands coupled to a detectable moiety described herein can be administered to a subject in a detectable quantity of a pharmaceutical composition containing the PSMA ligands coupled to a detectable moiety described herein or a pharmaceutically acceptable water-soluble salt thereof, to a patient. A "detectable quantity" means that the amount of the detectable compound that is administered is sufficient to enable detection of binding of the compound to the cancer cells. An "imaging effective quantity" means that the amount of the detectable compound that is administered is sufficient to enable imaging of binding of the compound to the cancer cells.

The PSMA ligands coupled to a detectable moiety described herein administered to a subject can be used to determine the presence, location, and/or distribution of cancer cells, i.e., PSMA expressing cancer cells or PSMA expressing neovaculature of the cancer cells, in an organ or body area of a patient. The presence, location, and/or distribution of the PSMA ligands coupled to a detectable moiety in the animal's tissue, e.g., brain tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the PSMA ligands coupled to a detectable moiety may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the PSMA ligands coupled to a detectable moiety may be administered to a subject to assess the distribution prostate cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of prostate on the tumor margin that are outside the tumor edge that appear to be grossly normal but are infiltrated by dispersing tumor cells upon histological examination.

The PSMA ligands coupled to a detectable moiety can be used in intra-operative imaging techniques to guide surgical resection and eliminate the "educated guess" of the location of the tumor by the surgeon. Previous studies have determined that more extensive surgical resection improves patient survival. Thus, the PSMA ligands coupled to a detectable moiety that function as diagnostic molecular imaging agents have the potential to increase patient survival rates.

In other embodiment, Y, $Y^1$, or $Y^2$ can be an anticancer agent, and the PSMA ligand coupled to the anticancer agent can be administered to a subject having or suspected having cancer, such as a PSMA expressing cancer (e.g., prostate cancer) to treat the cancer.

Examples of anticancer agents that can be directly or indirectly coupled to B include Taxol, Adriamycin, Dactinomycin, Bleomycin, Vinblastine, Cisplatin, acivicin; aclarubicin; acodazole hydrochloride; acronine; adozelesin;

aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atri- mustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; silicon phthalocyanine (PC4) sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosamOinoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anti-cancer agents can include the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Arnad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NC1), Resverastatin phosphate sodium, BPR-OY-007 (National Health Research Institutes), and SSR-250411 (Sanofi).

Still other anti-cancer agents include alkylating agents, such as nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.), antimetabolites, such as folic acid analog (e.g., methotrexate), or pyrimidine analogs (e.g., fluorouracil, floxouridine, Cytarabine), purine analogs (e.g., mercaptopurine, thioguanine, pentostatin, vinca alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

It will be appreciated, the detectable moieties, therapeutic agents, and/or theranostic agents need not be directly or indirectly conjugated to the PSMA ligand and can optionally be provided in a pharmaceutical compostion or preparation with the PSMA ligand.

The disclosed compounds and additional therapeutic agents, detectable moieties, and/or theranostic agents described herein can be administered to a subject by any conventional method of drug administration, for example, orally in capsules, suspensions or tablets or by parenteral administration. Parenteral administration can include, for example, intramuscular, intravenous, intraventricular, intraarterial, intrathecal, subcutaneous, or intraperitoneal administration. The disclosed compounds can also be administered orally (e.g., in capsules, suspensions, tablets or dietary), nasally (e.g., solution, suspension), transdermally, intradermally, topically (e.g., cream, ointment), inhalation (e.g., intrabronchial, intranasal, oral inhalation or intranasal drops) transmucosally or rectally. Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions may also be used to administer such preparations to the respiratory tract. Delivery can be in vivo, or ex vivo. Administration can be local or systemic as indicated. More than one route can be used concurrently, if desired. The preferred mode of administration can vary depending upon the particular disclosed compound chosen.

In specific embodiments, oral, parenteral, or system administration are preferred modes of administration for treatment.

The compounds can be administered alone as a monotherapy, or in conjunction with or in combination with one or more additional therapeutic agents. The term "in conjunction with" or "in combination with" indicates that the compound is administered at about the same time as the agent. The compound can be administered to the animal as part of a pharmaceutical composition comprising the compound and a pharmaceutically acceptable carrier or excipient and, optionally, one or more additional therapeutic agents. The compound additional therapeutic agent can be components of separate pharmaceutical compositions, which can be mixed together prior to administration or administered separately. The compound can, for example, be administered in a composition containing the additional therapeutic agent, and thereby, administered contemporaneously with the agent. Alternatively, the compound can be administered contemporaneously, without mixing (e.g., by delivery of the compound on the intravenous line by which the compound is also administered, or vice versa). In another embodiment, the compound can be administered separately (e.g., not admixed), but within a short time frame (e.g., within 24 hours) of administration of the compound.

The methods described herein contemplate single as well as multiple administrations, given either simultaneously or over an extended period of time. The compound (or composition containing the compound) can be administered at regular intervals, depending on the nature and extent of the inflammatory disorder's effects, and on an ongoing basis. Administration at a "regular interval," as used herein, indicates that the therapeutically effective amount is administered periodically (as distinguished from a one-time dose). In one embodiment, the compound is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased. Depending upon the half-life of the agent in the subject, the agent can be administered between, for example, once a day or once a week.

For example, the administration of the disclosed compound and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

The disclosed compound and/or additional therapeutic agent can be administered in a dosage of, for example, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day. Dosage forms (composition) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

The amount of disclosed compound and/or additional therapeutic agent administered to the subject can depend on the characteristics of the subject, such as general health, age, sex, body weight and tolerance to drugs as well as the degree, severity and type of rejection. The skilled artisan will be able to determine appropriate dosages depending on these and other factors using standard clinical techniques.

In addition, in vitro or in vivo assays can be employed to identify desired dosage ranges. The dose to be employed can also depend on the route of administration, the seriousness of the disease, and the subject's circumstances. Effective doses may be extrapolated from dose-response curves derived from in vitro or animal model test systems. The amount of the compound can also depend on the disease state or condition being treated along with the clinical factors and the route of administration of the compound.

For treating humans or animals, the amount of disclosed compound and/or additional therapeutic agent administered (in milligrams of compound per kilograms of subject body weight) is generally from about 0.1 mg/kg to about 100 mg/kg, typically from about 1 mg/kg to about 50 mg/kg, or more typically from about 1 mg/kg to about 25 mg/kg. In a preferred embodiment, the effective amount of agent or compound is about 1-10 mg/kg. In another preferred embodiment, the effective amount of agent or compound is about 1-5 mg/kg. The effective amount for a subject can be varied (e.g., increased or decreased) over time, depending on the needs of the subject.

The term "unit dose" refers to a physically discrete unit suitable as unitary dosage for the subject, each unit containing a predetermined quantity of active material that can produce the desired therapeutic effect in association with the required diluent; e.g., carrier or vehicle. In addition to the ingredients particularly mentioned above, the formulations of the present invention may include other agents conventional in the art having regard to the type of formulation in question.

The disclosed compound and/or additional therapeutic agent described herein can be administered to the subject in conjunction with an acceptable pharmaceutical carrier or diluent as part of a pharmaceutical composition for therapy. Formulation of the compound to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

A pharmaceutically acceptable carrier for a pharmaceutical composition can also include delivery systems known to the art for entraining or encapsulating drugs, such as anticancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

In other embodiments, the PSMA ligand can be conjugated to a nanoparticle to form a targeted nanoparticle that can used to deliver a therapeutic agent to a cancer cell of a subject or mammal. The targeted nanoparticle conjugates can target and transiently interact with, bind to, and/or couple with a cancer cell, such as a prostate cancer cell, and once interacting with, bound to, or coupled to the targeted cell or tissue advantageously facilitate delivery of a therapeutic agent within cell by, for example, receptor mediated endocytosis.

The targeted nanoparticle can be coated with a plurality of polymer chains and at least some of the polymer chains can coupled to at least one of the PSMA ligands described herein. Referring to FIG. 4, a first end of a polymer chain can be coupled and/or bound to a surface of the nanoparticle and a second opposite end that extends from the surface of the nanoparticle is coupled and/or bound to the PSMA ligands described herein. The PSMA ligand can allow the targeted nanoparticle conjugates to transiently interact, couple, and/or bind to the targeted cell or tissue.

The polymer coating can provide a protective shell that increases the hydrophilicity of the nanoparticle and biocompatibility of the targeted nanoparticle conjugates and postpone and/or delay clearance of the targeted nanoparticle conjugates after delivery to the subject by reticular-endothelium system. The polymer coating also acts as an amphiphilic reservoir that can adsorb and stabilize therapeutic agents in aqueous medium and/or blood of the subject without the need to modify the structure of the therapeutic agent. The adsorption and stabilization of the therapeutic agent allows the hydrophobic therapeutic agent to be delivered to the targeted cell or tissue by the targeted nanoparticle conjugates and minimizes side effects.

In some embodiments, the nanoparticles used to form the targeted nanoparticle conjugates are quantum dots, i.e., bright, fluorescent nanocrystals with physical dimensions small enough such that the effect of quantum confinement gives rise to unique optical and electronic properties. In certain embodiments, the nanoparticles are optically detectable nanoparticles, such as metal nanoparticles. Metals used to form the nanoparticles include, but are not limited to, gold, silver, iron, cobalt, zinc, cadmium, nickel, gadolinium, chromium, copper, manganese, palladium, tin, and alloys and/or oxides thereof. In some embodiments, the nanoparticles can be magnetic nanoparticles. "Magnetic particles" refers to magnetically responsive particles that contain one or more metals or oxides or hydroxides thereof.

In some embodiments, the nanoparticles can have an average diameter of about 1 nm to about 30 nm. In other embodiment, the nanoparticles can have an average diameter of about 5 nm or less. Nanoparticles with an average or nominal diameter of about 5 nm or less can be readily cleared from the subject by reticular endothelium system after delivery of the hydrophobic therapeutic agent to the targeted cell or tissue.

The polymers used to coat the nanoparticles can include natural proteins, such as bovine serum albumin (BSA), biocompatible hydrophilic polymers, such as polyethylene glycol (PEG) or a PEG derivative, phospholipid-(PEG), lipids, and carbohydrates, such as dextran. Coatings of polymer may be applied or assembled in a variety of ways, such as by dipping, using a layer-by-layer technique, by self-assembly, or conjugation. Self-assembly refers to a process of spontaneous assembly of a higher order structure that relies on the natural attraction of the components of the higher order structure (e.g., molecules) for each other. Self-assembly typically occurs through random movements of the molecules and formation of bonds based on size, shape, composition, or chemical properties.

In one embodiment, the polymer coating can include polyethylene glycol (PEG). The PEG can be a heterobifunctional PEG, such as COOH-PEG-SH (MW 3000), and/or a monofunctional PEG, such as PEG-SH (MW 5000), that can readily bind to the nanoparticle to coat the nanoparticle. In some embodiments, the nanoparticle can be coated with a mixture of hetero-bifunctional PEG, such as COOH-PEG-SH (MW 3000), and monofunctional PEG, such as PEG-SH (MW 5000). The mixture can range in percent composition of hetero-bifunctional PEG to mono-functional PEG of about 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, and 99:1 respectively.

The PSMA ligand can be coupled to the polymer chain prior to and/or after coupling of the polymer chain to the nanoparticle. The therapeutic agents, e.g., drugs and/or pharmacological compounds, can be loaded into and/or onto the polymer coating of the nanoparticles by encapsulation, absorption, adsorption, and/or non-covalent linkage of the therapeutic agent to or within the polymer matrix. The amount of therapeutic agent loaded onto the targeted nano-particle can be controlled by changing the size of the nanoparticles or the composition of the polymer coating. Release of the therapeutic agent from the targeted nanopar-ticle may occur by desorption, diffusion through the polymer coating matrix, or polymer wall, and/or nanoparticle ero-sion, which can all be controlled by the type of the nano-particle's polymer matrix, i.e., having it become swollen or degradable in the chosen microenvironment.

In some embodiments, the therapeutic agent can be a hydrophobic drug molecule that has a positive log P value. A hydrophobic therapeutic agent with a positive log P can be readily adsorbed into the polymer coating and stabilized in aqueous medium and/or blood of the subject without the need to modify the structure of the therapeutic agent. The adsorption and stabilization of the hydrophobic therapeutic agent allows the therapeutic agent to be delivered to the targeted cell or tissue and minimize side effects. In other embodiments, the hydrophobic therapeutic agent can have a log P of about 1 to about 5. In still other embodiments, the hydrophobic therapeutic agent can have a log P of about 1 to about 3.

Examples of hydrophobic therapeutic agents that can be adsorbed into the polymer coating and that have a positive log P are porphyrins and phthalocyanines, such as phthalo-cyanine 4 (Pc 4) Phthalocyanines, such as Pc4, can be used in photodynamic therapy (PDT). Pc4 is relatively photo-stable and virtually non-toxic. 5-amiolevulinic acid (5-ALA) leads to intracellular accumulation of fluorescent porphy-rins, which can be used to monitor tumor margins. 5-ALA has also been used for photodynamic therapy (PDT) of gliomas with some success (Stummer, W. et al. J Neuroon-col. 2008, 87(1):103-9.).

In some embodiments, the therapeutic agent is released from the nanoparticle once it reaches the target. Drug release can be induced by a thermodynamic driving force that drives the molecule from the amphiphilic environment of the polymer coating into any less polar site that may be offered for a long enough time. The therapeutic agent may be driven into the apolar center of the cell membranes and subse-quently taken up into the targeted cell.

In some embodiments, the targeted nanoparticle conju-gates can be formulated and used in a photodynamic therapy to treat cancer or tumor (e.g., brain cancer or tumors). Photodynamic therapy (PDT) is a site specific treatment modality that requires the presence of a photosensitizer, light, and adequate amounts of molecular oxygen to destroy targeted tumors (Grossweiner, Li, The sicence of photo-therapy. Springer: The Netherlands, 2005). Upon illumina-tion, a photoactivated sensitizer transfers energy to molecu-lar oxygen that leads to the generation of singlet oxygen ($O^2$) and other reactive oxygen species (ROS), which initiate apoptosis and oxidative damage to cancer cells. Only the cells that are exposed simultaneously to the PDT drug (which is non-toxic in the dark) and light are destroyed while surrounding healthy, non-targeted and nonirradiated cells are spared from photodamage. Furthermore, the fluores-cence of the photosensitizer molecules enables simultaneous diagnostic optical imaging that can be used to guide the PDT cancer treatment.

In some embodiments, the targeted nanoparticle conju-gates formulated for PDT treatment method can include PEGylated gold nanoparticles that are modified with a PSMA ligand described herein and that are conjugated to a PDT therapeutic agent (e.g., Pc4) that is spacially encaged and photophysically quenched through adsorption on the PEGylated nanoparticles. The nanoparticles can include gold nanoparticles that have a diameter about 5 nm or less to allow efficient excretion via renal clearance after delivery of the hydrophobic PDT therapeutic agent. The PEGylated nanoparticles can each have an average or nominal diameter of about 38 nm. About 10 to about 50, e.g., about 20-30, hydrophobic PDT therapeutic agents can be adsorbed on each nanoparticle.

The targeted nanoparticles containing the PDT therapeu-tic agent can be administered to a subject with cancer by (e.g., prostate cancer) systemic administration, such as intra-venous administration. Upon administration, the targeted nanoparticle conjugates can localize to and/or accumulate at the site of the targeted tumor or cancer. Transient binding and/or interaction of the targeted nanoparticle conjugates with the prostate cancer cells allows the PDT therapeutic agent to be delivered to and take up by the targeted prostate cells by, for example, endocytosis with virtually no uptake of the nanoparticles. This uptake is specific to the targeted cancer cells, which allows selective targeting of the cancer cells in the subject by the targeted nanoparticle conjugates.

Following administration and localization of the targeted nanoparticle conjugates as well as uptake of the PDT therapeutic agent by the targeted cancer cells, the targeted cancer cells can be exposed to therapeutic amount of light that causes cancer cell damage and/or suppression of cancer cell growth. The light, which is capable of activating the PDT therapeutic agent can delivered to the targeted cancer cells using, using for example, semiconductor laser, dye laser, optical parametric oscillator or the like. It will be appreciated that any source light can be used as long as the light excites the hydrophobic PDT therapeutic agent.

In other embodiments, the PSMA ligand can be conju-gated to a stabilized nanobubble to form a targeted stabilized nanobubble. The targeted stabilized nanobubbles can be used as multifunctional and/or theranostic platforms for diagnostic imaging, drug therapy, and gene therapy, chemo-therapy. The stabilized nanobubble can include a membrane that defines an internal void. The internal void can include at least one gas. The membrane can include at least one lipid and at least one nonionic triblock copolymer that is effective to control the size of the nanobubble without compromising in vitro and in vivo echogenicity of the nanobubble.

In some embodiments, the nonionic triblock copolymer can include at least one poloxamer. The poloxamer can have a molecular, for example, of about 1100 Daltons to about 3000 Daltons. The concentration of nonionic triblock copo-lymer in the lipid nanobubble can be about 0.06 mg/ml to about 1 mg/ml. The gas can have a low solubility in water and include, for example, a perfluorocarbon, such as per-fluoropropane, carbon dioxide, and air. The nanobubble can have a size that facilitates extravasation of the nanobubble in cancer therapy or diagnosis. For example, the nanobubble can have a diameter or size of about 50 nm to about 800 nm (or about 50 nm to about 400 nm).

In still other embodiments, the PSMA ligand can be conjugated to a muli-component nano-chain to form a targeted nano-chain. The targeted nano-chain can be used as a multifunctional platform for diagnostic imaging, drug therapy, gene therapy, and chemotherapy. The nanochain can include at least three nanoparticles linked together to form the nanochain. At least one nanoparticle of the nanochain has an asymmetric surface chemistry defined by asymmetrically disposed first linkers and second linkers. The nanoparticles can be linked to form the nanochain by linking first linkers and/or second linkers disposed on separate nanoparticles.

In some embodiments, the nanoparticles can have an average or nominal diameter of about 1 nm to about 50 nm and the nanochain can have a length less than about 200 nm and a width about 50 nm or less. The nanoparticles forming the nanochain can be the same or different and be selected from the group consisting of a metal nanoparticle, lipidic nanoparticle, polymer nanoparticle, liposome, or dendrimer.

The nanochain can include multiple PSMA ligands described herein. The PSMA ligands can be linked to surfaces of the nanoparticles and the spacing between the nanoparticles can be controlled to facilitate targeting of the nanoparticles to cells of a subject. The spacing and location of the PSMA ligand on each nanoparticle can be controlled to facilitate delivery, targeting, and/or therapeutic efficacy of the nanochain when administered to a subject.

In some embodiments the nanochain can include at least two metal nanoparticles. At least one of the metal nanoparticles can be linked to a liposome, lipidic nanoparticle, or polymer nanoparticle that includes an imaging agent or therapeutic agent. The metal nanoparticles of the nanochain when administered to a subject can be responsive to energy, from a remote source that is effective to release the imaging agent or therapeutic agent from the liposome, lipidic nanoparticle, or polymer nanoparticle. In one example, the energy can be radiofrequency (RF) energy that causes mechanical oscillation or resonance of the metal nanoparticles that is effective to release the therapeutic agent or imaging agent from the liposome, lipidic nanoparticle, or polymer nanoparticle. The RF energy effective to release the therapeutic agent or imaging agent can be an amount less than that required to induce a substantial or significant localized temperature increase in the subject.

The following examples are for the purpose of illustration only and are not intended to limit the scope of the claims, which are appended hereto.

Example 1

In this Example, we developed prostate cancer selective nanoparticles with theranostic capabilities. Specifically, we developed small molecule-based PSMA ligands to target Pc4-containing gold nanoparticles to prostate tumors that overexpress PSMA surface protein. This nanoparticle has been designed to contain and deliver a photodynamic therapeutic (PDT) agent, Pc4, which is both fluorescent (40% fluorescence yield) and a potent cancer therapeutic (50% singlet oxygen yield) that can be activated by application of near infrared (NIR) light of 670 nm wavelength. During surgery the fluorescent Pc4 delivered by this nanoparticle can be exploited to visually differentiate the tumor from surrounding normal tissues (e.g., nerves), which do not take it up, providing image guidance and the ability to judge the extent of cancer infiltration. Upon completion of the prostatectomy, light of a specific wavelength can be used to excite Pc4 PDT resulting in free radical generation and robust killing of the remaining cancer tissues that were not removed by the surgical procedure.

Figure 2:
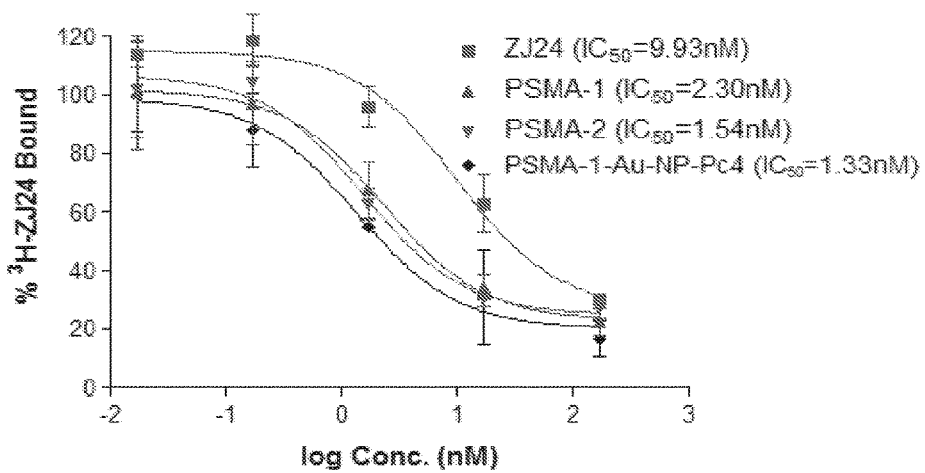
FIG. 2 illustrates a plot showing the results of a competition binding study for different PSMA ligands. PSMA-expressing PC3pip cells were incubated with different concentrations of ligands in the presence of 12 nM of 3H-labeled ZJ24. Cell associated uptake was measured. Error bars+/−SD.

We developed a 2'5'-oligoadenylate (2'5'-A)-containing PSMA ligand, RBI1033, which had significantly improved binding affinity compared to the parent urea-based ligand (S)-2-(3-((S)-5-amino-1-carboxypentyl)ureido)pentanedioic acid (ZJ24) an analog of which is in clinical trials for prostate cancer imaging. We hypothesized that the binding affinity of RBI1033 may be due to the charge-charge interaction through the negatively charged phosphate backbone and interaction of aromatic amino acid residues of PSMA with the adenine moiety. However, further in vivo studies with RBI1033 showed no difference in uptake between tumors that expressed PSMA and those that did not. A possible explanation was that the 2'5'-A moiety was not stable in vivo. Based on our charge-charge interaction hypothesis, we synthesized a presumably more stable peptide-based PSMA ligand, PSMA-1 (FIG. 1), by mimicking the negative charge and hydrogen bonding of the 2'5'-A moiety using amino acids. A lysine residue was attached at the C-terminal end of the molecule so that large fluorescent moieties could be attached. Competitive binding assays using tritiated ZJ24, FIG. 2, showed that the new ligand, now called PSMA-1, had an $IC_{50}$=2.3 nM which was much better than that measured for ZJ24, $IC_{50}$=9.3 nM. Interestingly, coupling PSMA-1 with an IR800 dye (Li-Cor Biosciences, Lincoln, Nebr.) to form PSMA-2 further increased its affinity to the PSMA receptor reducing its $IC_{50}$ to 1.54 nM, FIG. 2.

Figure 3:
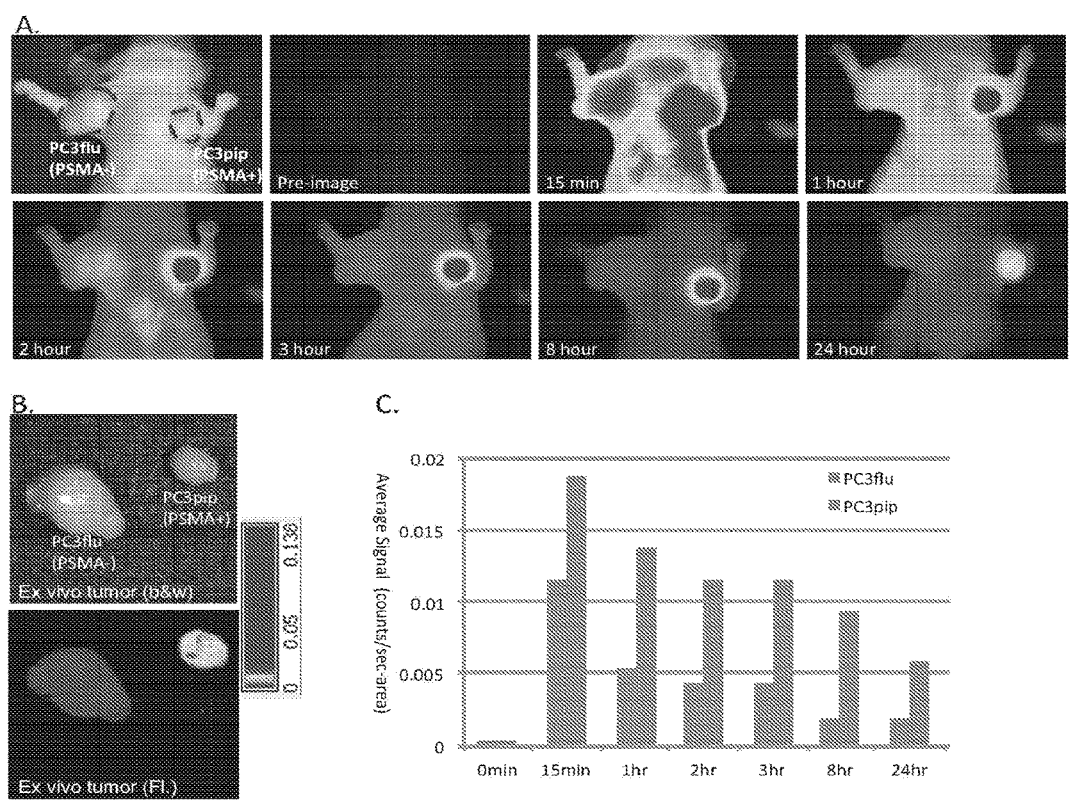
FIGS. 3(A-C) illustrate the results of in vivo imaging of PSMA-2. A nude mouse bearing both PC3pip and PC3flu tumors was injected with 1 nmole of PSMA-2. At the indicated times the mouse was imaged using the Maestro imaging device. A) In vivo imaging at different times; B) Tumors were removed and imaged ex vivo 24 hours after injection; C) ROI corresponding to the circles in (A) were used to acquire signal for quantification. Data was expressed as counts/sec-area. All images in (A) and (B) are at the same scale.

Next, we tested the fluorescent PSMA-2 for in vivo targeting to tumors overexpressing PSMA. Mice were implanted with both PSMA-expressing (PC3pip cells) or PSMA negative tumor cells (PC3flu cells). At various times after IV injection of the PSMA-2 probe animals were subjected to fluorescence imaging using a Maestro Imaging device (CRI now Perkin Elmer). Within 3 hours imaging demonstrated specific localization of PSMA-2 to PSMA-expressing tumors but not to PSMA negative tumors, FIG. 3, verifying the in vivo feasibility of using this ligand to drive targeted delivery of nanoparticles to tumors.

We next exploited our expertise in Au nanoparticles to generate PSMA-1-labeled Au—NP-Pc4. In this system, 5 nm gold nanoparticles were utilized to provide good renal clearance. PSMA-1 was reacted with 5 k PEG to generate PSMA-1-PEG5KSH. The Au NPs reacted with a mixture of PSMA-1-PEG5K-SH and PEG5K-SH and Pc4 was finally adsorbed to the particle to generate PSMA-1-Au—NP-Pc4 conjugates, FIG. 4. The final PSMA-1-Au—NP-Pc4s had an average hydrodiameter of 33 nm. Adsorption of Pc4 and conjugation of PSMA-1-PEG to the particles was monitored by absorbance and gel electrophoresis, respectively, FIG. 5. Based on the absorption at 520 nm and 678 nm we calculated that there were 20 Pc4 molecules/Au—NP. We first measured the affinity of the targeted nanoparticles for PSMA using our competitive binding assay. The PSMA-1-Au—NP-Pc4 showed a greater affinity for the PSMA protein ($IC_{50}$=1.33 nM) than the unconjugated PSMA-1 did ($IC_{50}$=2.30 nM) and was inline with the affinity measured for the PSMA-2 ligand ($IC_{50}$=1.54 nM), FIG. 5, black diamonds.

Figure 6:
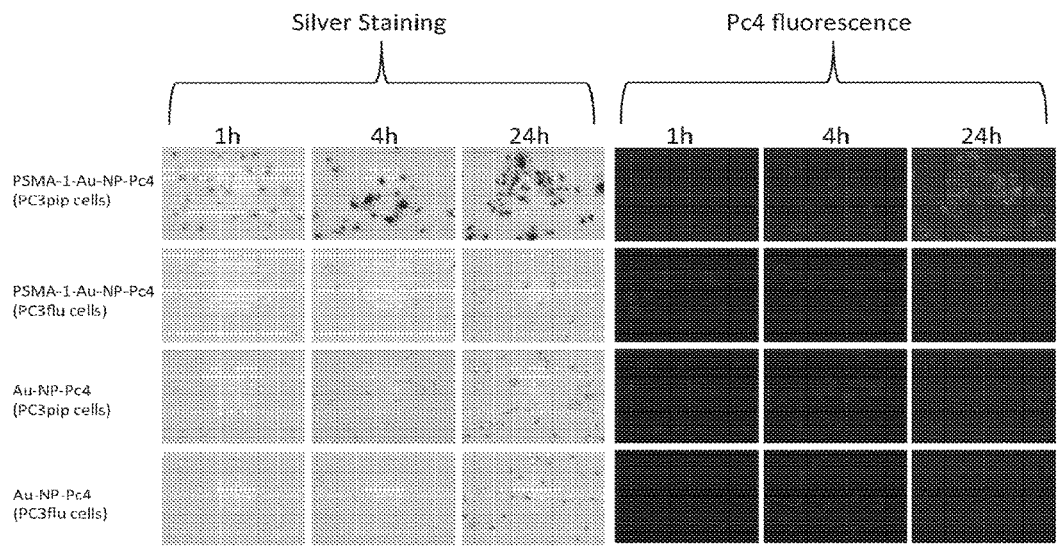
FIG. 6 illustrates the results of a cellular uptake study of targeted and non-targeted Au—NP-Pc4. Either PSMA-1-Au—NP-Pc4 or Au—NP-Pc4 was administered to PC3pip, which overexpress PSMA, or PC3flu cells, which express little PSMA, and the uptake of Pc4 and Au nanoparticles was visualized. PC4 fluorescence was visualized using a microscope outfitted with filters for Cy5 emission and Au nanoparticles were visualized using white light after enhancement with silver staining. Only PSMA-1-Au—NP-Pc4 added to PSMA expressing cells delivered Pc4 and particles to the cells.
Figure 7:
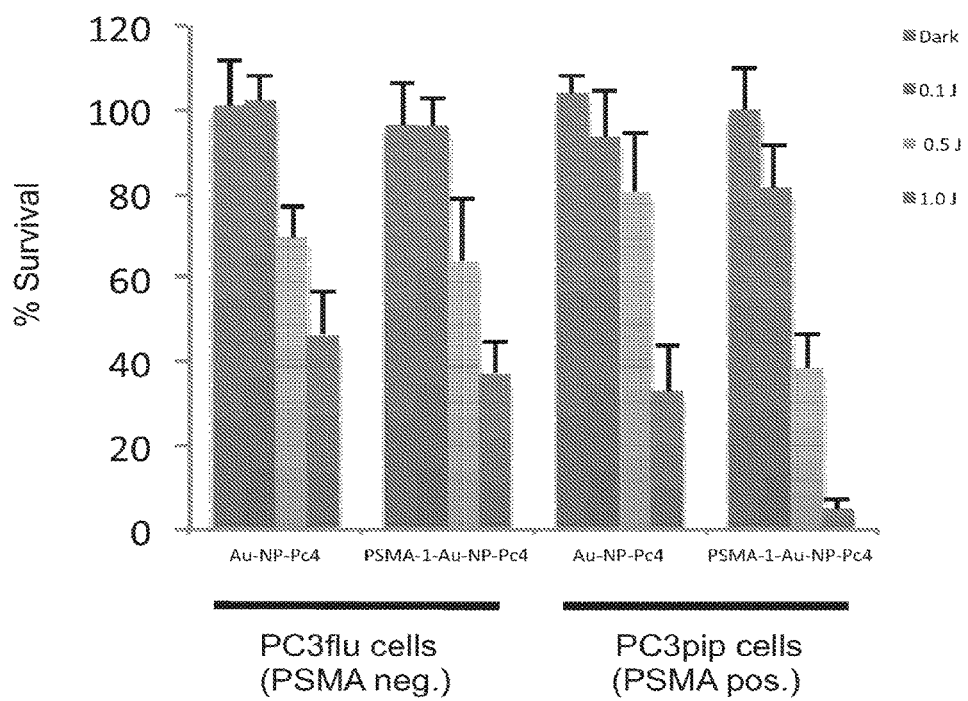
FIG. 7 illustrates a graph showing efficacy of PSMA-1-Au—NP-Pc4 for killing prostate cancer cell lines. PSMA-expressing or nonexpressing PC3 cells were incubated with either targeted or non-targeted Au—NP-Pc4 for 4 hours. Following washing, cells were exposed to different doses of light and percent of surviving cells was calculated 24 hours later using a MTT assay. PSMA-1-Au—NP-Pc4 are more efficient at killing PSMA-expressing cells than non-targeted nanoparticles and more selective for PSMA-expressing cells. Error bars=SD.

Finally, we used the non-targeted and PSMA-targeted gold nanoparticles in vitro to treat PC3pip (PSMA-positive cells) or PC3flu (PSMA-negative cells) and assessed both uptake and cell killing associated with activation of the Pc4 after exposure to light. Using silver staining to enhance Au nanoparticle detection we were able to demonstrate significantly higher gold uptake in PSMA-expressing PC3pip cells than that in PSMA-negative PC3flu cells, FIG. 6. The uptake of Pc4 was observed by its fluorescence under the microscope and correlated well with the cell associate Au—NP assessed by silver staining. Both sets of cells were then subjected to light exposure to activate delivered Pc4. FIG. 7 demonstrates that PSMA-positive cells were more completely killed by the light than PSMA-negative cells which took up little to no Pc4. All these results indicated that active targeting has been achieved by modifying the Au-NPs with PSMA-1 ligand.

Example 2

This Example describes PSMA-targeted near infrared imaging probes that can help define extra-capsular invasion of prostate cancer and help differentiate between diseased and normal tissues during surgery, improving prostatectomies. The results demonstrate that these probes can bind efficiently to PSMA. These probes can be used for diagnosis and image-guided surgery for prostate cancer.

Methods and Materials
General (S)-2-(3-((S)-5-amino-1-carboxypentyl)ureido)pentanedioic acid was custom made by Bachem Bioscience Inc. (Torrance, Calif.). N—[N—[(S)-1,3-dicarboxypropyl]carbamoyl]-S-[3H]-methyl-L-cysteine was custom made by GE Healthcare Life Sciences (Pittsburgh, Pa.). H-Glu(OtBu)—OtBu was purchase from Bachem Bioscience Inc. Fmoc-Rink Amide MBHA resin, Fmoc-(D)Glu(OtBu)—OH, Fmoc-Lys(Mtt)-OH, Fmoc-Ahx-OH and 2-(6-Chloro-1H-benzotriazole-1-yl)-1,1,3,3-tetramethylaminium hexafluorophosphate (HCTU) were purchased from Peptides International Inc (Louisville, Ky.). Fmoc-Glu-α-OtBu (Glu') was from Novabiochem (Damstadt, Germany). Fmoc-Amc-OH was from ABX Advanced Biochemical Compounds, Germany. All the other chemicals were purchased from Sigma-Aldrich Inc., St. Louise, Mo., USA.

Synthesis of Glu-CO-Glu'-Amc-Ahx-Glu-Glu-Glu-Lys-NH$_2$ (PSMA-1): PSMA-1 was synthesized manually using standard Fmoc chemistry. Generally, peptide was synthesized at 0.2 mmol scale starting from C-terminal Fmoc-rink amide MBHA resin. Fmoc-deprotection at each cycle was carried out using 20% pipperidine in DMF. Coupling reactions were carried out using 3.3 equiv of Fmoc-amino acids in DMF activated with 3.3 equiv of HCTU and 5 equiv of diisopropylethylamine (DIPEA) in DMF. These steps were repeated each time with an amino acid added. After the peptide sequence Fmoc-Glu'-Amc-Ahx-Glu-Glu-Glu-Lys(Mtt) was built on the resin, the Fmoc group of N-terminal amino acid Glu' was deprotected by 20% pipperidine. Then, a chloroform solution containing 3 eq of H-Glu(OtBu)—OtBu mixed with 2.5 eq of DIPEA were prepared. The solution is then added slowly to 0.25 eq triphosgene in chloroform over 10 minutes at room temperature. After 15 minute incubation to allow for isocyanate formation, the reaction mixture was mixed with Glu'-Amc-Ahx-Glu-Glu-Glu-Lys on rink amide resin pre-swollen in chloroform with 2.5 eq of DIPEA. After the reaction was complete, the resin was washed with DMF and then dichloromethane and dried. The peptide was cleaved from resin by TFA/water/triisopropylsilane (950:25:25). The cleaved peptide was purified by preparative HPLC. The products were ascertained by high resolution matrix-assisted laser desorption/ionization mass (MALDI-MS) spectra from an Applied Biosystem 4800 MALDI TOF/TOF Analyzer in positive ion mode. Retention time: 19.0 min. MALDI MS: $C_{48}H_{74}N_{10}O_{20}$, 1087.5 (found); 1087.1 (calculated).

Synthesis of PSMA-1-IR800 (PSMA-2)

Coupling of PSMA-1 to IRDye800-NHS ester (Li-Cor Biosciences, Lincoln, Nebr.) was performed in DMF. Basically, 100 nmol of PSMA-1 was dissolved in 100 uL of DMF, to which 50 nmol of IRDye800-NHS ester in DMF was added. The reaction was carried out at room temperature for 3 hrs. The crude was then purified by preparative HPLC. Yield: 67%. Retention time: 22.4 min. MALDI-MS: $C_{92}H_{126}N_{12}O_{34}S_4$, 2071.8 (found); 2072.3 (calculated)

Synthesis of PSMA-1-Cy5.5 (PSMA-3)

The compound was synthesized using the same method as the synthesis of PSMA-2 using Cy5.5 NHS ester (Lumiprobe Life Science Solutions, Hallandale Beach, Fla.). Yield: 73%. Retention time: 38.8 min. MALDI-MS: $C_{86}H_{115}N_{12}O_2$, 1651.7 (found); 1651.8 (calculated).

High Performance Liquid Chromatography (HPLC)

High Performance Liquid Chromatography (HPLC) was performed on a Shimadzu HPLC system equipped with a SPD-20A prominence UV/visible detector and monitored at a wavelength at 220 nm. Preparative HPLC was achieved using Luna 5μ C18(2) 100A column (250 mm×10 mm×5 μm, Phenomenex, Torrance, Calif.) at a flow rate of 3.0 ml/min. Analytical HPLC was performed using an analytical Luna 5μ C18(2) 100A column (250 mm×4.6 mm×5 m, Phenomenex) at a flow rate of 1.0 mL/min. Gradient used was 5%-55% Acetonitrile against 0.1% trifluoroacetic acid over 30 minutes.

Cell Culture

Retrovirally transformed PSMA positive PC3pip cells and transfection control PC3flu cells were obtained from Dr. Michel Sadelain (Laboratory of Gene Transfer and Gene Expression, Gene Transfer and Somatic Cell Engineering Facility, Memorial-Sloan Kettering Cancer Center, New York, N.Y.). Cells were grown at 37° C. and 5% $CO_2$ under a humidified atmosphere. Cells were maintained in RPMI1640 medium supplemented (Invitrogen Life Technology, Grand Island, N.Y.) with 2 mM L-glutamine and 10% Fetal Bovin Serum.

Competitive Binding Assay

PC3pip cells ($5\times10^5$) were incubated with different concentrations of ligands in the presence of 12 nM N—[N—[(S)-1,3-dicarboxypropyl]carbamoyl]-S-[3H]-methyl-L-cysteine ($^3$H-ZJ24) in a total volume of 300 μL for 1 hour at 37° C. The mixture was centrifuged at 3,000 g for 5 min at 4° C., then washed three time with 500 μL of cold PBS. Finally, 4 mL of EcoLume™ cocktail (MP Biomedicals, Solon, Ohio) was added, and radioactivity was counted by scintillation counter. The concentration required to inhibit 50% of binding is determined ($IC_{50}$) by GraphPad Prism 3.0.

In Vitro Cellular Uptake Studies

Pc3pip and PC3flu cells were plated on coverslips at about 70% confluency. After incubated overnight to promote adherence, cells were treated with 1 μM of PSMA-1-Cy5.5. After incubated for various times (5 minutes, 30 minutes, 1 hour and 4 hours), cells were washed three times with PBS, fixed with 4% paraformaldehyde, counterstained with 2-(4-amidinophenyl)-6-indolecarbamidine dihydrochloride (DAPI), mounted with Fluor-Mount aqueous mounting solution, sealed with nail polish, and observed using Leica DM4000B fluorescence microscopy (Leica Microsystem Inc, Buffalo Grove, Ill.).

Mouse Tumor Xenograph Models

All animal procedures were performed according to Institutional Animal Care and Use Committee (IACUA)

approved protocols. Animals were fed on a special rodent diet (Harlan Laboratories, Inc.) to reduce auto fluorescence. For flank tumor xerographs, six to eight weeks old athymic nude mice were implanted subcutaneously with $1 \times 10^6$ of PSMA-negative PC3flu and PSMA-positive PC3pip cells in 100 μL matrigel under the right and left upper chester respectively. Animals were observed every other day until tumors reached at about 10 mm in diameter. For othotopic tumor model, six to eight weeks old athymic nude mice were first anesthetized by intraperitoneal injection of 50 mg/kg ketamine/xyazine. A transverse incision was made in the lower abdomen just anterior to the bulbourethral gland. Abdominal muscle will be incised. The bladder dome was gently grasped and pulled posteriorly to expose the dorsal-lateral prostate, which was identified as a well-vascularized area at the dorsal side of the bladder neck. A $28^{1/2}$-gauge insulin needle was inserted into dorsal lateral prostate glands to deliver 10 to 20 μl cell suspension ($5 \times 10^7$ cells/ml). A well-localized bleb within the injected prostate lobe is a sign of a technically satisfactory injection. The incision in the abdominal wall was closed. After four weeks, animals were ready for imaging experiment.

In Vivo NIR Imaging Studies

Imaging was performed on Maestro In vivo Imaging system (Perkin-Elmer, Waltham, Mass.) with each mouse received 1 nmol of NIR probe in PBS through tale vein injection. For mice bearing flank tumors, imaging was performed at different time points under appropriate channel. During imaging, the temperature of imaging bed was adjusted to 37° C. Mice received inhalation of isofluorane through a nose cone attached to the imaging bed. Mice were image over 5 days post injection, after which, the mice were sacrificed by cervical dislocation and tissues such as liver, kidneys, tumors, heart, bladder and urinary gland were harvested for ex vivo imaging. Fluorescent molecular tomographic (FMT) images were obtained using the FMT2500 device (Perkin-Elmer, Waltham, Mass.) and three-dimensional reconstructions of fluorescent signals were acquired using the accompanying software, TrueQuant. Quantification of fluorescent signals was obtained by calibration of PSMA-1-IR800 and PSMA-1-Cy5.5 using appropriate channel. For othotopic mouse models, mice were imaged by Maestro Imaging System at 24 hours post tale vein injection of 1 nmol of PSMA-1-Cy5.5. After that, mouse was euthonized, and the abdomen was opened to expose the tumor. The mouse was imaged again. Finally, tumor was harvest for ex vivo imaging.

Results

Chemistry

The PSMA-1 ligand was synthesized completely on solid phase Rink Amide Resin and then cleaved by 95% trifluoroacetic acid, purified by HPLC and characterized by TOF-MALDI-MS. PSMA-1 (FIG. 1) contains three D-glutamic acid to mimic the negative charges on the phosphate backbone of 2-5A, and the D isomer was selected to improve the peptide's in vivo stability. A lysine was introduced at the C-terminal of the peptide to allowing future coupling with other agents. IRDye800 is a water soluble dye with excitation/emission wavelength at 774 nm/789 nm and extinction coefficient at $2.4 \times 10^5$ $M^{-1}$ $cm^{-1}$. Cy5.5 is very hydrophobic and not water soluble with excitation/emission wavelength at 673 nm/707 nm. Its extinction coefficient is $2.1 \times 10^5$ $M^{-1}cm^{-1}$. Both dyes are near infrared emitting dyes and can avoid the natural background fluorescence interference of biomolecules, providing a high contrast between target and background tissues. PSMA-1-IR800 and PSMA-1-Cy5.5 were obtained by reaction of PSMA-1 with the commercially available dye IRDye800 NHS ester or Cy5.5 NHS ester in PBS at room temperature. All compounds were purified by HPLC and characterized by MALDI-TOF MS to confirm the structure. The attachment of IRDye800 to PSMA-1 shifted it HPLC retention time from 19.0 min to 22.4 min; while the attachment of Cy5.5 to PSMA800 shifted the retention time further to 38.8 min. The longer HPLC retention time of PSMA-1-Cy5.5 than PSMA-1-IR800 indicated that PSMA-1-Cy5.5 is much more hydrophobic than PSMA-1-IRDye800.

Competition Binding Studies

To determine the binding affinity of the new ligands synthesized, we performed competition binding experiments. The experiments were carried out by incubating PSMA positive PC3pip cells with 12 nM tritium-labeled ZJ24 ($^3$H-ZJ24) and vary concentrations of new PSMA probes. The results are summarized in Table 1. It was found that the rationally designed new PSMA ligand PSMA-1 has a binding affinity more than 4.3 fold better ($IC_{50}$=2.30 nM) than the parent ligand ZJ24 ($IC_{50}$=9.93 nM). Interestingly, inclusion of IR800 further improved the $IC_{50}$ of PSMA-1-IR800 to 1.53 nM; different from this, introduction of Cy5.5, which did not show much effect to the binding affinity of PSMA-1-Cy5.5 ($IC_{50}$=2.07 nM).

TABLE 1

Summary of competition binding results of PSMA ligands

| | ZJ24 | PSMA-1 | PSMA-1-IR800 | PSMA-1-Cy5.5 |
|---|---|---|---|---|
| $IC_{50}$ (nM) | 9.93 ± 0.07 | 23.0 ± 0.06 | 1.53 ± 0.14 | 2.07 ± 0.13 |

In Vitro Cellular Uptake Results

The in vitro uptake experiment was performed to compare the cellular uptake of PSMA-1-Cy5.5 in PSMA positive PC3pip and PSMA negative PC3flu cells. The experiment was only done with PSMA-1-Cy5.5 due to lack of appropriate excitation channel for PSMA-1-IR800. FIGS. 2A-H are typical fluorescence images of PC3pip and PC3flu cells after incubated with PSMA-1-Cy5.5 for different times. Fluorescence in PC3pip cells were observed 15 minutes after treated with PSMA-1-Cy5.5, the signal increased as incubation time increased. In contrast to the PC3pip cells, no fluorescence was observed in PC3flu cells at the same exposure time. To test if the binding of PSMA-1-Cy5.5 to PSMA is specific, the cells were incubated PSMA-1-Cy5.5 and 10 fold excess amount of ZJ24 (FIGS. 8I-J). It was found that the fluorescence in PC3pip cells was completely blocked with co-incubation of ZJ24, indicating specific binding.

NIR Imaging Results

In order to evaluate the in vivo behavior of our PSMA-1-Dye conjugates, a mouse model bearing both PSMA-positive PC3pip and PSMA-negative PC3flu tumors was used. The NIR probe was injected through tail vein injection and mouse was imaged at designated time points by Maestro Imaging as well as Fluorescence Molecular Tomography. When mice were injected with PSMA-1-IR800, increased uptake in PSMA-positive PC3pip tumor was observed as early as 5 min post injection (FIG. 9A). The signal in PC3pip tumors kept increasing, reached highest at 4 hours post injection and then gradually went down. At early time points, the signals in the mice bladder were very strong, even higher that in PC3pip tumors; however, the signal in the bladder was minimal at later time points, indicating that the probe PSMA-1-IR800 was mainly excreted from the urinary extraction tract. Immediately following Meastro Imaging, mice were imaged by FMT to get 3D quantification of the probes (FIG. 9C). The FMT data indicated that at 4 hours post injection, the amount of PSMA-1-IR800 in PC3pip tumors (71.2±14.4 pmol) was significantly higher than that in PC3flu tumors (7.5±1.8 pmol). Five days post injection, mice were sacrificed and organs were harvested for ex vivo imaging. Bright fluorescent signal was observed in PC3pip tumor; some signal was observed in mouse kidneys, but was much lower compared to that in PC3pip tumor; signals in other organs including PC3flu tumor were minimal (FIG. 9B).

In contrast, when mice were injected with 1 nmol of PSMA-1 Cy5.5, selective uptake in PSMA positive PC3pip tumor was initially observed 4 hours post injection; the signal intensity in PC3pip tumors reached highest at the time point 24 hours posted injection and then remained virtually unchanged for 120 hours (FIG. 10A). FMT 3D quantification of the signals in the tumors indicated that at 24 hours post injection, the amount of PSMA-1-Cy5.5 in PC3pip tumors (50.8±2.6 pmol) was more than 10 fold higher than that in PC3flu tumors (4.5±0.8 pmol) (FIG. 10C). The excellent selectivity of PSMA-1-Cy5.5 was also demonstrated by ex vivo imagining, in which the signals in PC3pip tumor were significantly higher than in other organs including the kidneys (FIG. 10B).

To further demonstrate that PSMA-1-Cy5.5 can selectively target PSMA in prostate, we tested it in mice bearing othotopic PC3pip tumor. In vivo imaging with mice bearing flank tumors has shown that highest tumor uptake of PSMA-1-Cy5.5 was observed 24 hours post injection, therefore, mice was sacrificed at 24 hours after injection of 1 nmol of PSMA-1-Cy5.5. The mouse abdomen was opened to expose the tumor for image. Significant fluorescent signal was observed on the tumor, while little fluorescence was observed in the background (FIG. 11A, 11C). Ex vivo imaging of the PC3pip tumor demonstrated comparable fluorescent signal to that obtained by in vivo imaging (FIG. 11B, 5D). These data again confirmed that PSMA-1-Cy5.5 can recognize and bind to othotopic PC3pip tumors.

A major concern of conjugation bulky dye into the ligand is that the dye might significantly interfere with the interaction between the ligand and receptor, causing loss of binding affinity, but this didn't happen to our conjugates. PSMA-1-IR800 and PSMA-1-Cy5.5 showed comparable or even improved binding affinity than PSMA-1 itself. The active site of PSMA contains S1' and S1 pockets. The S1' pocket is occupied by the glutamate residue of the ligand. The remaining part of ligand is aligned along the S pocket. S1 pocket contains a 20 Å deep tunnel projected towards the surface of PSMA. With the long peptide based linker, the fluorophores might have already situated outside of the active site, therefore, do not have much effect on their binding affinity. In vitro cellular uptake experiments with PSMA-1-Cy5.5 showed that it can selectively bind to PSMA-expressing PC3pip cells, but not to PSMA-non-expressing PC3flu cells. In the presence of excess amount of ZJ24, the binding of PSMA-1-Cy5.5 to PC3pip cells was blocked, indicating the binding is specific to PSMA. In in vivo experiments, both PSMA-1-IRdye800 and PSMA-1-Cy5.5 showed excellent binding selectivity to PSMA-positive PC3pip tumors with more than 10 fold of difference between PC3pip and PC3flu tumors. Interestingly, the two probes showed distinctively different pharmacokinetic behaviors. The amount of PSMA-1-IR800 reached highest in PSMA-positive PC3pip tumors at 4 hours post injection, while it took PSMA-1-Cy5.5 24 hours to reach highest amount in PC3pip tumors. PSMA-1-IR800 was excreted faster from the body, while PSMA-1-Cy5.5 had a longer retention time. Comparing the structure of IRDye800 and Cy5.5, there are three more negatively charged sulfate group in IRDye800, therefore, Cy5.5 is less polar and much more hydrophobic than IRDye800. This may be the reason that the two probes had different pharmacokinetics. We got excellent results with both our PSMA-1-NIR dye probes, further proving the rational design of our PSMA ligand. The ability of PSMA-1-Cy5.5 to detect prostate tumors was also demonstrated by mouse othotopic models. All these data suggested the high selectivity and specificity of our PSMA-1-NIR dye probes to PSMA expressing tumors.

All references cited herein, including patents, patent applications, papers, text books, and the like, and the references cited therein, to the extent that they are not already, are hereby incorporated herein by reference in their entirety. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Having described the invention, we claim:

1. A method of treating cancer in a subject in need thereof, the method comprising:

administering to the subject a therapeutically effective amount of a compound having the following formula (I):

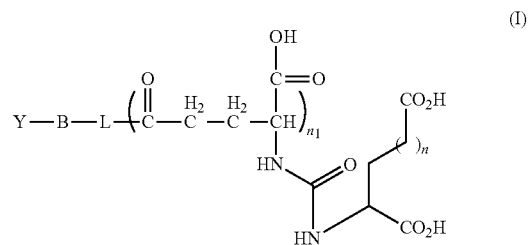

wherein:

n and $n^1$ are each independently 1, 2, 3, or 4;

L comprises at least one ring selected from the group consisting of an optionally substituted 4 to 7 membered nonaromatic heterocyclic ring and an optionally substituted C4-C7 cycloalkyl ring;

B comprises at least one glutamic acid residue; and

Y is a H of B or includes at least one of a detectable moiety, therapeutic agent, or a theranostic agent that is directly or indirectly linked to B.

2. The method of claim 1, wherein Y is selected from the group consisting of an imaging agent, anticancer agent, or combination thereof.

3. The method of claim 1, wherein B has the following formula:

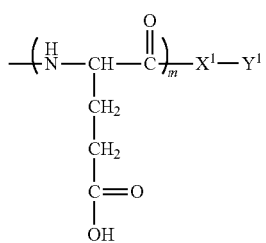

wherein m is 1, 2, 3, or 4, $X^1$ is an amino acid, and $Y^1$ is a H of $X^1$ or includes at least one of an amino acid, peptide, detectable moiety, therapeutic agent, or theranostic agent that is directly or indirectly linked to $X^1$.

4. The method of claim 1, the compound having the general formula:

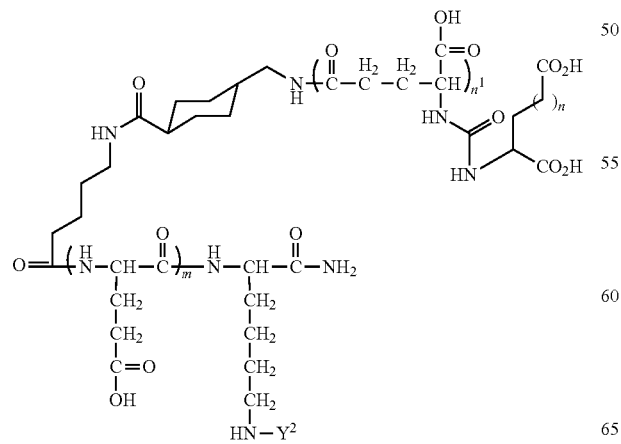

wherein m, n, and $n^1$ is 1, 2, 3, or 4; n and $n^1$ are each independently 1, 2, 3, or 4; and $Y^2$ is a H or includes at least one of an amino acid, peptide, detectable moiety, therapeutic agent, or theranostic agent.

5. The method of claim 1, wherein Y is a (PEGylated) nanoparticle that is directly or indirectly linked to B, and at least one anti-cancer agent coupled to the surface of the nanoparticle.

6. The method of claim 5, wherein the anti-cancer agent comprising Phthalocyanine 4.

7. The method of claim 1, wherein the compound has the following formula:

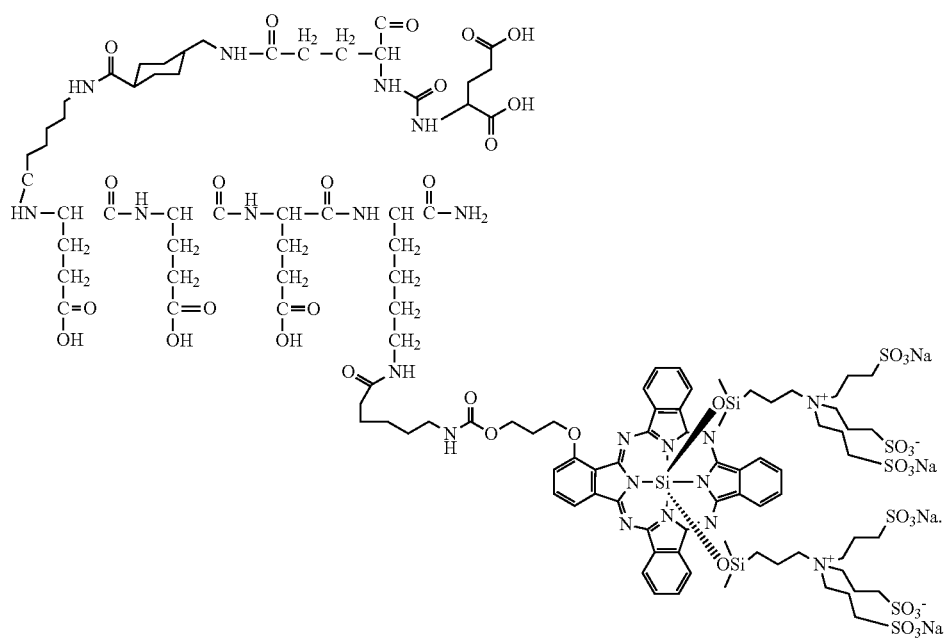

8. The method of claim 1, wherein the compound has the following formula:
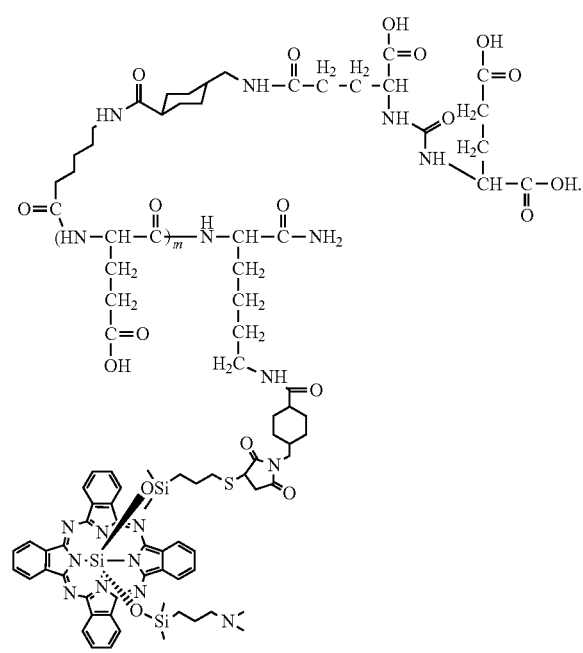
9. The method of claim 1, wherein the compound has the following formula:
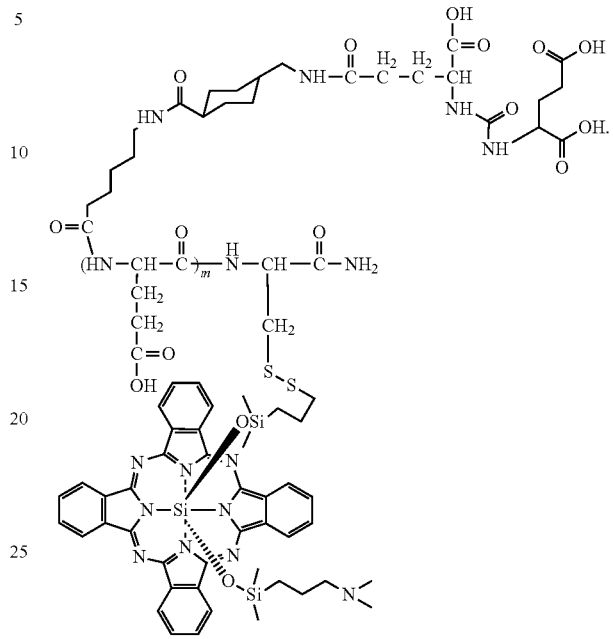
* * * * *